(12) United States Patent
Angibaud et al.

(10) Patent No.: US 8,889,866 B2
(45) Date of Patent: Nov. 18, 2014

(54) TETRAHYDROPHENANTHRIDINONES AND TETRAHYDROCYCLOPENTAQUINOLINONES AS PARP AND TUBULIN POLYMERIZATION INHIBITORS

(75) Inventors: Patrick René Angibaud, Fontaine-Bellenger (FR); Laurence Anne Mevellec, Louviers (FR); Bruno Roux, Saint Leger du Bourg-Denis (FR); Pierre-Henri Storck, Kent (GB); Christophe Meyer, Les Authieux sur le Port Saint (FR); Jorge Eduardo Vialard, Brussels (BE)

(73) Assignee: Janssen Pharmaceutica, NV (BE)

( * ) Notice: Subject to any disclaimer, the term of this patent is extended or adjusted under 35 U.S.C. 154(b) by 654 days.

(21) Appl. No.: 12/934,753

(22) PCT Filed: Mar. 26, 2009

(86) PCT No.: PCT/EP2009/053598
§ 371 (c)(1),
(2), (4) Date: Dec. 14, 2010

(87) PCT Pub. No.: WO2009/118382
PCT Pub. Date: Oct. 1, 2009

(65) Prior Publication Data
US 2011/0263622 A1 Oct. 27, 2011

(30) Foreign Application Priority Data

Mar. 27, 2008 (EP) ..................................... 08153432

(51) Int. Cl.
*C07D 221/12* (2006.01)
*C07D 401/06* (2006.01)
*A61K 31/4353* (2006.01)

(52) U.S. Cl.
CPC .......... *C07D 401/06* (2013.01); *A61K 31/4353* (2013.01); *C07D 221/12* (2013.01)
USPC ........................................... 546/79; 514/290

(58) Field of Classification Search
USPC ........................................... 546/79; 514/290
See application file for complete search history.

(56) References Cited

U.S. PATENT DOCUMENTS

| | | |
|---|---|---|
| 3,274,194 A | 9/1966 | Hayao et al. |
| 3,753,988 A | 8/1973 | Rodway et al. |
| 3,879,393 A | 4/1975 | Havera |
| 3,919,425 A | 11/1975 | Vidrio |
| 4,335,127 A | 6/1982 | Vandenberk et al. |
| 5,028,606 A | 7/1991 | Venet et al. |
| 5,118,684 A | 6/1992 | Sugimoto et al. |
| 5,151,421 A | 9/1992 | Venet et al. |
| 5,177,075 A | 1/1993 | Suto et al. |
| 5,231,184 A | 7/1993 | Stokbroekx et al. |
| 5,304,560 A | 4/1994 | Shimazaki et al. |
| 5,374,637 A | 12/1994 | Van Daele et al. |
| 6,344,449 B1 | 2/2002 | Rudolf et al. |
| 6,583,144 B2 | 6/2003 | Ohkura et al. |
| 6,635,642 B1 | 10/2003 | Jackson et al. |
| 7,115,630 B2 | 10/2006 | Mabire et al. |
| 7,498,325 B2 | 3/2009 | Rudolf et al. |
| 7,928,104 B2 | 4/2011 | Mabire et al. |
| 8,198,448 B2 | 6/2012 | Albrecht et al. |
| 2001/0036946 A1 | 11/2001 | Rudolf et al. |
| 2002/0002174 A1 | 1/2002 | Nieduzak et al. |
| 2003/0069231 A1 | 4/2003 | Rudolf et al. |
| 2003/0130505 A1 | 7/2003 | Zhi et al. |
| 2003/0225268 A1 | 12/2003 | Bunnelle et al. |
| 2004/0077667 A1 | 4/2004 | Matsuoka et al. |
| 2004/0176361 A1 | 9/2004 | Fujio et al. |
| 2005/0256000 A1 | 11/2005 | Schaper et al. |
| 2008/0039480 A1 | 2/2008 | Kennis et al. |
| 2008/0269234 A1 | 10/2008 | Gandhi et al. |
| 2009/0048259 A1 | 2/2009 | Austin et al. |
| 2009/0163480 A1 | 6/2009 | Rudolf et al. |
| 2009/0292121 A1 | 11/2009 | Morioka et al. |
| 2012/0046274 A1 | 2/2012 | Mabire et al. |

FOREIGN PATENT DOCUMENTS

| | | |
|---|---|---|
| DE | 1006423 | 4/1957 |
| DE | 2258561 A | 6/1973 |
| EP | 0013612 B1 | 11/1983 |
| EP | 156433 | 10/1985 |

(Continued)

OTHER PUBLICATIONS

Dorwald F. A. Side Reactions in Organic Synthesis, 2005, Wiley: VCH, Weinheim p. IX of Preface. preface and p. 1-9.*

(Continued)

*Primary Examiner* — Rita Desai

(57) ABSTRACT

The present invention provides compounds of formula (I), their use as inhibitors of tubulin polymerization and their use as PARP inhibitors as well as pharmaceutical compositions comprising said compounds of formula (I)

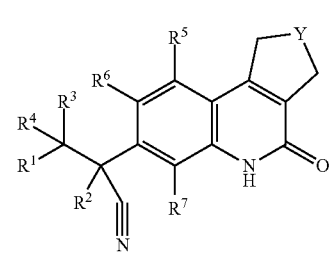

(I)

wherein $R^1$, $R^2$, $R^3$, $R^4$, $R^5$, $R^6$, $R^7$ and Y have defined meanings.

8 Claims, No Drawings

(56) References Cited

FOREIGN PATENT DOCUMENTS

| | | |
|---|---|---|
| EP | 0156433 B1 | 10/1985 |
| EP | 0229391 B1 | 7/1987 |
| EP | 0391462 A1 | 10/1990 |
| EP | 391462 A1 | 10/1990 |
| EP | 0638567 | 2/1995 |
| EP | 0638567 A1 | 2/1995 |
| EP | 0371564 B1 | 7/1995 |
| EP | 0669919 B1 | 9/1995 |
| EP | 1026160 A1 | 8/2000 |
| EP | 0885190 B1 | 5/2003 |
| EP | 1355888 | 10/2008 |
| FR | 2436781 | 5/1980 |
| GB | 732581 A | 6/1955 |
| GB | 1062357 | 3/1967 |
| GB | 1062357 A | 3/1967 |
| JP | 59-076082 | 4/1984 |
| JP | 60-120872 | 6/1985 |
| JP | 60-120872 A | 6/1985 |
| JP | 60-226862 | 11/1985 |
| JP | 62-234065 | 10/1987 |
| JP | 10007572 | 1/1998 |
| JP | 10007572 A | 1/1998 |
| JP | 10-330377 | 12/1998 |
| JP | 10-330377 A | 12/1998 |
| JP | 2002-515072 | 3/1999 |
| JP | 2002-515072 A | 3/1999 |
| JP | 2000-505100 | 4/2000 |
| JP | 2000-505100 A | 4/2000 |
| JP | 2000191659 | 7/2000 |
| JP | 2000191659 A | 7/2000 |
| JP | 2002-535409 | 8/2000 |
| JP | 2002-535409 A | 8/2000 |
| JP | 2002284699 | 10/2002 |
| JP | 2002284699 A | 10/2002 |
| WO | WO 91/12006 A2 | 8/1991 |
| WO | WO 93/22309 A1 | 11/1993 |
| WO | WO 9322309 A1 | 11/1993 |
| WO | WO 94/19342 A1 | 9/1994 |
| WO | WO 95/24379 | 9/1995 |
| WO | WO 95/24379 A1 | 9/1995 |
| WO | WO 98/11128 A1 | 3/1998 |
| WO | WO 99/11649 A2 | 3/1999 |
| WO | WO 99/29687 A1 | 6/1999 |
| WO | WO 00/44755 A1 | 8/2000 |
| WO | WO 02/28837 A1 | 4/2002 |
| WO | WO 02/36599 A1 | 5/2002 |
| WO | WO 02/48117 A1 | 6/2002 |
| WO | WO 03/015785 A1 | 2/2003 |
| WO | WO 03/039460 A2 | 5/2003 |
| WO | WO 03/055865 A1 | 7/2003 |
| WO | WO 03/080581 A1 | 10/2003 |
| WO | WO 03/082350 A2 | 10/2003 |
| WO | WO 03/101985 A1 | 12/2003 |
| WO | WO 2004/043950 A1 | 5/2004 |
| WO | WO 2005/004801 A2 | 1/2005 |
| WO | WO 2005/054199 A1 | 6/2005 |
| WO | WO 2005/054201 A1 | 6/2005 |
| WO | WO 2005/054209 A1 | 6/2005 |
| WO | WO 2005/054210 A1 | 6/2005 |
| WO | WO 2005/058843 A1 | 6/2005 |
| WO | WO 2005/097750 A1 | 10/2005 |
| WO | WO 2005/117876 A1 | 12/2005 |
| WO | WO 2006/003146 A1 | 1/2006 |
| WO | WO 2006/003147 A1 | 1/2006 |
| WO | WO 2006/003148 A1 | 1/2006 |
| WO | WO 2006/003150 A1 | 1/2006 |
| WO | WO 2006/089177 A2 | 8/2006 |
| WO | WO 2007/025009 A2 | 3/2007 |
| WO | WO 2007/087684 A1 | 8/2007 |
| WO | WO 2007/095628 A1 | 8/2007 |
| WO | WO 2008/107478 A1 | 9/2008 |
| ZA | 72/8536 A | 11/1972 |
| ZA | 7208536 A | 9/1973 |

OTHER PUBLICATIONS

Albert, J.M., et al., "Inhibition of Poly(ADP-Ribose) Polyerase Enhances Cell Death and Improves Tumor Growth Delay in Irradiated Lung Cancer MODels", Clin Cancer Res, (2007), vol. 13, No. 10, pp. 3033-3042.

Ali, M.M., et al., "Synthesis and Antimicrobial Activities of Some Novel Quinoxalinone Derivatives", Molecules, (2000), vol. 5, No. 6, pp. 864-873.

Ame, J.C., et al., "PARP-2, A Novel Mammalian DNA Damage-Dependent Poly(ADP-Ribose) Polymerase", Journal of Biological Chemistry, (1999), vol. 274, No. 25, pp. 17860-17868.

Ame, J.C., et al., "The PARP Superfamily", BioEssays, (2004), vol. 26, No. 8, pp. 882-893.

Bellasio, E., et al., "Antihypertensives. N-1$H$-Pyrrol-1-YL-3-Pyridazinamines", J. Med. Chem., (1984), vol. 27, No. 8 pp. 1077-1083.

Blackburn, W., et al., "The Preparation of 3-Methyl-6- and -7-Carboxy-2-Quinoxalones", Journal of Organic Chemistry, ((1961), vol. 26, pp. 2805-2809.

Bloch, W., et al., "Poly-Adenosine Diphosphate-Ribose Polymerase Inhibition for Myocardial Protection: Pathopysiologic and Physiologic Considerations", Journal of Thoracic and Cardiovascular Surgery, vol. 128, No. 2, pp. 323-324.

Bonne, D., et al., "4',6-Diamidino-2-Phenylindole, a Fluorescent Probe for Tubulin and Microtubules", Journal f Biological Chemistry, (1985), vol. 260, No. 5, pp. 2819-2825.

Calabrese, C.R., et al., "Anticancer Chemosensitization and Radiosensitization by the Novel Poly(ADP-Ribose) Polymerase-1 Inhibitor AG14361", Journal of the National Cancer Institute, (2004), vol. 96, No. 1, pp. 56-67.

Cardozo, M.G., et al., "Conformational Analyses and Molecular-Shape Comparisons of a Series of Indanone-Benzylpiperidine Inhibitors of Acetylcholinesterase", J. Med. Chem., (1992), vol. 35, pp. 590-601.

Cockcroft, X., et al., "Phthalazines 2: Optimisation and Synthesis of Novel Potent Inhibitors of Poly(ADP-Ribose)Polymerase", Bioorganic & Medicinal Chemistry Letters, (2006), vol. 16, pp. 1040-1044.

Costantino, G., et al., "Modeling of Poly(ADP-Ribose)Polymerase (PARP) Inhibitors. Docking of Ligands and Quantitative Structure-Activity Relationship Analysis", J. Med. Chem., (2001), vol. 44, pp. 3786-3794.

Cuzzocrea, S., "Shock Inflammation and PARP", Pharmacological Research, (2005), vol. 52, pp. 72-82.

Dastmalchi, S., et al., "Molecular Modelling of Human Aldehyde Oxidase and Identification of the Key Interactions in the Enzyme-Substrate Complex", Daru, J. Faculty of Pharm., (2005), vol. 13, No. 3, pp. 82-93.

Dörwald, F.Z., "Side Reactions in Organic Synthesis": A Guide to Successful Synthesis Design, Weinheim: Wiley-VCH Verlag GmbH & Co. KGaA, (2005), Preface.

Golbraikh, A., et al., "Validation of Protein-Based Alignment in 3D Quantitative Structure-Activity Relationships With CoMFA Models", Eur. J. Med. Chem., (2000), vol. 35, pp. 123-136.

Guery, S., et al., "Synthesis of 4-Aryl-1-(4-Methylpiperazin-1-yl)Phthalazines by Suzuki-Type Cross-Coupling Reaction", Synthesis, (2001), No. 5, pp. 699-701.

Gupta, C.M., et al., "Drugs Acting on the Central Nervous System. Syntheses of Substituted Quinazolones and Quinazolines and Triazepino- and Triazocinoquinazolones", Journal of Medicinal Chemistry (1968), vol. 11, No. 2, pp. 392-395.

Habon, T., et al., "The Effect of Carvedilol on Enhanced ADP-Ribosylation and Red Blood Cell Membrane Damage Caused by Free Radicals", Cardiovascular Research, (2001), vol. 52, p. 153-160.

Hayao, S., et al., "New Sedative and Hypotensive 3-Substituted 2,4(1H,3h-)-Quinazolinediones", Journal of Medicinal Chemistry, (1965), vol. 8, pp. 807-811.

Hazard, P.R., et al., "De Quelques Actions Pharmacologiques Exercees Par Des Derives De L'Orthoprocainamide", Thérapie, (1965), vol. XX, pp. 1043-104.

Herndon, J.L., et al., "Ketanserin Analogues: Structure-Affinity Relationships for 5-$HT_2$ and 5-$HT_{1C}$ Serotonin Receptor Binding", J. Med. Chem., (1992), vol. 35, pp. 4903-4910.

(56) References Cited

OTHER PUBLICATIONS

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 3, pp. 681-687.
Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 5, pp. 1286-1291.
Horvath, E.M., et al., "Poly(ADP-Ribose) Polymerase as a Drug Target for Cardiovascular Disease and Cancer: An Update", Drug News Perspect, (2007), vol. 20, No. 3, pp. 171-181.
Jordan, V.C., "Tamoxifen: A Most Unlikely Pioneering Medicine", Nature Reviews, (2003), vol. 2, pp. 205-213.
Katoh, A., et al., "Synthesis of Quinoxaline Derivatives Bearing the Styryl and Phenylethynyl Groups and Application to a Fluorescence Derivatization Reagent", Heterocycles, (2000), vol. 52, No. 2, pp. 911-920.
Kormendy, K., et al., "Aminophthalazinone Derivatives, V Synthesis of 4-Hydrazino-1-(2-H)Ophthalazinones, I", Acta Chimica Academiae Scientiarum Hungaricae, (1979), vol. 102, No. 1, pp. 39-50.
Kornet, M.J., et al., "Synthesis of 3-Amino-2,4(1$H$,3$H$)-Quinazolinediones for Testing as Anticonvulsants", J. Heterocyclic Chem., (1984), vol. 21, No. 5, pp. 1533-1535.
Kulcsar, G., et al., Synthesis and Study of New 4-Quinazolinone Inhibitors of the DNA Repair Enzyme Poly(ADP-Ribose) Polymerase (PARP), ARKIVOC, XX,XX, (2003), vol. 2003, No. Part V, pp. 121-131.
Larner, A.J., "Poly(ADP-Ribose) Polymerase Inhibitors in the Prevention of Neuronal Cell Death", Expert Opin. Ther. Patents, (2002), vol. 12, No. 4, pp. 481-487.
Li, J.H., et al., "PARP Inhibitors", IDrugs, (2001), vol. 4, No. 7, pp. 804-812.
Lord, C.J., et al., "Targeted Therapy for Cancer Using PARP Inhibitors", Current Opinion in Pharmacology, (2008), vol. 8, pp. 363-369.
Meier, H.L., et al., "Alterations in Human Lymphocyte Dna Caused by Sulfur Mustard Can Be Mitigated by Selective Inhibitors of Poly(ADP-Ribose) Polymerase", Biochimica et Biophysica Acta, (1998), vol. 1404, pp. 367-376.
Miller, B.A., "Inhibition of TRPM2 Function by PARP Inhibitors Protects Cells From Oxidative Stress-Induced Death", British Journal of Pharmacology, (2004), vol. 143, pp. 515-516.
Nguewa, P.A., et al., "Poly(ADP-Ribose) Polymerases: Homology, Structural Domains and Functions. Novel Therapeutical Applications", Progress in Biophysics & Molecular Biology, (2005), vol. 88, pp. 143-172.
Oliver, A.W., et al., "Crystal Structure of the Catalytic Fragment of Murine Poly(ADP-Ribose) Polymerase-2", Nucleic Acids Research, (2004), vol. 32, No. 4, pp. 456-464.
Schreiber, V., et al., "Poly(ADP-Ribose) Polymerase-2 Is Required for Efficient Base Excision DNA Repair in Association With PARP-1 and XRCC1", Journal of Biological Chemistry, (2002), vol. 277, No. 25, pp. 23028-23036.
Szabo, G., et al., "Poly(ADP-Ribose Polymerase Inhibition Protects Against Myocardial and Endothelial Reperfusion Injury After Hypothermic Cardiac Arrest", Journal of Thoracic and Cardiovascular Surgery, (2003), vol. 126, No. 3, pp. 651-658.
Takai, H., et al., "Synthesis of Piperidine Derivatives With a Quinazoline Ring System as Potential Antihypertensive Agents", Chem. Pharm. Bull, (1986), vol. 34, No. 5, pp. 1907-1916.
Tasatargil, A., et al., "Poly(ADP-Ribose) Polymerase Inhibition Prevents Homocysteine-Induced Endothelial Dysfunction in the Isolated Rat Aorta", Pharmacology, (2004), vol. 72, pp. 99-105.
Tentori, L., et al., "Chemopotentiation by PARP Inhibitors in Cancer Therapy", Pharmacological Research, (2005), vol. 52, pp. 25-33.
Vippagunta, S.R., et al., "Crystalline Solids", Advanced Drug Delivery Reviews, (2001), vol. 48, pp. 3-26.
Virag, L., et al., "The Therapeutic Potential of Poly(ADP-Ribose) Polymerase Inhibitors", Pharmacological Reviews, (2002), vol. 54, No. 3, pp. 375-429.

Weltin, D., et al., "Effect of 6(5H)-Phenanthridinone, An Inhibitor of Poly(ADP-Ribose) Polymerase, on Cultured Tumor Cells", Oncology Research, (1994), vol. 6, No. 9, pp. 399-403.
Wolff, M.E., Burger's Medicinal Chemistry, 4$^{th}$ ed., Part I The Basis of Medicinal Chemistry, (1980), pp. 336-337.
Yolles, S., et al., "Quinoxaline Studies. I. The Preparation of 2-Hydroxy-3-Methyl-6-Methoxyquinoxaline and 2-Hydroxy-3-Methyl-7-Methoxyquinoxaline", Journal of the American Chemical Society, (1949), vol. 71, pp. 2375-2377.
Zhang, J., "PARP Inhibition: A Novel Approach to Treat Ischaemia/ Reperfusion and Inflammation-Related Injuries", Emerging Drugs, (1999), vol. 4, pp. 209-221.
"Cancer definition", http://www.medterms.com/script/main/art.asp?articlekey=2580, accessed Nov. 27, 2007.
The Merck Index, 13$^{th}$ Ed., p. 670, monograph for "Ethyl Alcohol"© 2001 by Merck and Co., Inc.
"Prostate Cancer Prevention", http://www.cancer.gov/cancertopics/pdq/prevention/prostate/Patient, accessed Apr. 9, 2010.
EDAN30610, Jun. 8, 2011.
Database CA 'Online! Chemical Abstracts Service, Columbus, Ohio, US; 2002, Tatsuno, Toru et al: "PARP Inhibitors for Treatment of Retinal Degeneration or Chemotherapy-Induced Cell Injury" XP002348719 retrieved from STN Database accession No. 2002:747681, relevant to claim 1-12.
Patent Abstracts of Japan, vol. 1998, No. 5, Apr. 30, 1998—& JP 10007572 A (Sumitomo Pharmaceut Co Ltd), Jan. 13, 1998 '0046!, Formula 14 abstract.
Database WPI 'Online! Derwent Publications Ltd., London, GB; XP002347462, retrieved from WPI accession No. 1970-18449R, ;see RN 27631-66-9:3-(piperidin-1-yl-propyl)-1H-quinazoline-2,4-dione, abstract & JP 45007058B (Sankyo) Jul. 6, 1967.
Finney, D. J., "Graded Response: The Linear Dosage-Response Curve", Probit Analysis, 2nd Edition, Chapter 10 (1962), Cambridge Publishing Press, 16 page article.
Bonne, D., et al., "4'6-Diamidino-2-phenylindole, a Fluorescent Probe for Tubulin and Microtubules", Journal of Biological Chemistry, vol. 260, No. 5 (1985), pp. 2819-2825.
Horvath, E., et al. "Poly(ADP-ribose) Polymerase as a Drug Target for Cardiovascular Disease and Cancer: An Update", Drug News Perspectives, vol. 20, No. 3 (2007), pp. 171-181.
Amé, J-C., et al. "The PARP Superfamily", BioEssays vol. 26 (2004), pp. 882-893.
Li, J. et al., "PARP Inhibitors", IDrugs, vol. 4, No. 7 (2001), pp. 804-812.
Nguewa, P., et al., "Poly(ADP-Ribose) Polymerases: Homology, Structural Domains and Functions. Novel Therapeutical Applications", Progress in Biophysics & Molecular Biology, vol. 88 (2005), pp. 143-172.
Tentori, L., et al. "Poly(ADP-ribose)polymerase (PARP) Inhibition or PARP-1 gene Deletion Reduces Angiogenesis", European Journal of Cancer, vol. 43, No. 14 (2007), pp. 2124-2133.
Weltin, D., et al. "Effect of 6(5H)-Phenanthridinone, an Inhibitor of Poly(ADP-ribose) Polymerase, on Cultured Tumor Cells", Oncology Research, vol. 6, No. 9 (1994), pp. 399-403.
International Search Report for corresponding Patent Application No. PCT/EP2009/053598 mailed May 19, 2009.
International Search report for Application No. PCT/EP2004/013162 mailed Mar. 18, 2005.
International Search report for Application No. PCT/EP2004/013163 mailed Apr. 20, 2005.
International Search report for Application No. PCT/EP2004/013164 mailed Mar. 14, 2005.
International Search report for Application No. PCT/EP2004/013165 mailed Mar. 24, 2005.
International Search report for Application No. PCT/EP2005/053029 mailed Oct. 7, 2005.
International Search report for Application No. PCT/EP2005/053030 mailed Oct. 24, 2005.
International Search report for Application No. PCT/EP2005/053031 mailed Oct. 25, 2005.
International Search report for Application No. PCT/EP2008/052764 mailed Aug. 12, 2008.

(56) References Cited

OTHER PUBLICATIONS

International Search report for Application No. PCT/EP2008/064243 mailed Mar. 30, 2009.
International Search report for Application No. PCT/EP2009/053598 mailed May 19, 2009.
International Search report for Application No. PCT/EP2009/053604 mailed May 8, 2009.
Calabrese et al., Journal of the National Cancer Institute, 2004, 96(1), pp. 56-69.
Bernard et al., "Automated docking of 82 N-benzylpiperidine derivatives to mouse acetylcholinesterase and comparative molecular field analysis with 'natural' alignment.", Journal of Computer-Aided Molecular Design, 1999, 13(4), pp. 355-371.
Borisy et al., "Systematic Discovery of Multicomponent Therapeutics.", PNAS, Jun. 24, 2003, pp. 7977-7982, vol. 100(13).
CAS Registry Nos. 464169-24-2, 464169-25-3, 223587-51-7 abstract; figure 24-&JP 2002 284699 A (Sumitomo Pharmaceuticals Co., Ltd., Japan) Oct. 3, 2002.
Darchen et al., "Ketanserin binds to the monoamine transporter of chromaffin granules and of synaptic vesicles.", Molecular Pharmacology, 1988, 33(6), pp. 672-677.
Kormendy, K. and Ruff, F., "Aminophthalazinone Derivatives, VII* Reaction of Chlorophthalazinone With Secondary Amines Study of the Steric Effect, I ." *Acta Chimica Academiae Scientiarum Hungaricae*, 1981, pp. 155-166, vol. 106(2).
Kormendy, K. and Ruff, F., "Aminophthalazinone Derivatives, VII. Methods for the Synthesis of Imidazo[2,1-α]Phthalazine and Pirimido[2,1-α]Phthalazine Ring Systems, I.", *Acta Chimica Hungarica*, 1983, pp. 65-82, vol. 112(1).
Leysen et al., "Non-serotonergic [3H]ketanserin binding sites in striatal membranes are associated with a dopac release system on dopaminergic nerve endings.", European Journal of Pharmacology, 1987, 134(3) 373-375.
Pailer et al., "Syntheisis of quinoxalone derivatives.", Monatshefte fuer Chemie, 1962, pp. 1005-1010, vol. 93.
Peters et al., "Basis for effective combination cancer chemotherapy with antimetabolites.", Pharmacology & Therapeutics, 2000, pp. 227-253, vol. 87.
Tentori, L., et al. "Poly(ADP-ribose)polymerase (PARP) Inhibition or PARP-1 gene Deletion Reduces Angiogenesis", European Journal of Cancer, vol. 43, No. 14 (2007) pp. 2124-2133.

* cited by examiner

TETRAHYDROPHENANTHRIDINONES AND TETRAHYDROCYCLOPENTAQUINOLINONES AS PARP AND TUBULIN POLYMERIZATION INHIBITORS

CROSS REFERENCE TO RELATED APPLICATIONS

This application is a national stage of PCT Application No. PCT/EP2009/053598, filed Mar. 26, 2009, which claims priority for EPO Patent Application No. 08153432.3, filed Mar. 27, 2008, all of which are hereby incorporated by reference in their entirety.

FIELD OF THE INVENTION

The present invention relates to inhibitors of PARP and tubulin polymerization and provides compounds and compositions containing the disclosed compounds.

Moreover, the present invention provides methods of using the disclosed PARP and tubulin polymerization inhibitors for instance as a medicine.

BACKGROUND OF THE INVENTION

The nuclear enzyme poly(ADP-ribose) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1 and TANK-2. PARP is also referred to as poly(adenosine 5'-diphospho-ribose) polymerase or PARS (poly(ADP-ribose) synthetase).

Tankyrases (TANKs) were identified as components of the human telomeric complex. They have also been proposed to have roles in regulation of the mitotic spindle and in vesicle trafficking and they may serve as scaffolds for proteins involved in various other cellular processes. Telomeres, which are essential for chromosome maintenance and stability, are maintained by telomerase, a specialized reverse transcriptase. TANKs are (ADP-ribose)transferases with some features of both signalling and cytoskeletal proteins. They contain the PARP domain, which catalyses poly-ADP-ribosylation of substrate proteins, the sterile alpha motif, which is shared with certain signalling molecules and the ANK domain, which contains 16 to 24 ankyrin repeats, also present in the cytoskeletal protein ankyrin. The ANK domain interacts with a variety of different proteins, including the telomeric protein, Telomere Repeat binding Factor-1 (TRF-1). These proteins were therefore named TRF1-interacting, ankyrin-related ADP-ribose polymerases (TANKs).

One function of TANKs is the ADP-ribosylation of TRF-1. Human telomere function is regulated by a complex of telomere associated proteins that includes the two telomere-specific DNA binding proteins, TRF-1 and TRF-2. TRF-2 protects chromosome ends, and TRF-1 regulates telomere length. ADP-ribosylation inhibits the ability of TRF-1 to bind to telomeric DNA. This poly-ADP-ribosylation of TRF-1 releases TRF-1 from the telomeres, thereby opening up the telomeric complex and allowing access to telomerase. Therefore, TANKs function as positive regulators of telomere length, allowing elongation of the telomeres by telomerase.

Other roles for TANKs are suggested by the identity of proteins with which they interact—the insulin-responsive aminopeptidase, the Mcl1 proteins (which are members of the Bcl-2 family), the Epstein-Barr nuclear antigen-1, the nuclear and mitotic apparatus protein and the cytoplasmic and heterochromatic factor TAB 182- and its various subcellular localizations (nuclear pores, Golgi apparatus and mitotic centrosomes).

Tankyrase-2 (TANK-2) differs from tankyrase-1 (TANK-1) in that it lacks an N-terminal HPS domain (comprised of homopolymeric repeats of His, Pro and Ser residues), found in TANK1. However, it probably has some overlapping functions with tankyrase-1, given that both proteins have similar sub-cellular localizations, associate with each other and bind many of the same proteins.

PARP-1 is a major nuclear protein of 116 kDa consisting of three domains: an N-terminal DNA binding domain containing two zinc fingers, an automodification domain and a C-terminal catalytic domain. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, HMG proteins, topoisomerases, DNA and RNA polymerases, DNA ligases, $Ca^{2+}$- and $Mg^{2+}$-dependent endonucleases and single-strand break-repair and base-excision repair factors. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold. The resulting poly(ADP-ribose) production has three consequences: first, DNA-damage-induced poly(ADP-ribosyl)ation of the N- and C-terminal tails of histone H1 and H2B or the selective interaction of these proteins with free or PARP-1 bound poly(ADP-ribose) contributes to the relaxation of the 30-nm chromatin fibre and increases the access to breaks; second, it signals the occurrence and the extent of DNA damage so that the cell can establish an adaptive response according to the severity of the injury (DNA repair or cell suicide); third, it mediates the fast recruitment of single-strand break-repair and base-excision repair factors.

Single strand breaks (SSBs) occur spontaneously in all cells. In the absence of PARP-1 activity these SSBs may be converted to double strand breaks (DSBs) during replication that can lead to collapse of the replication forks. DSBs are identified by their epigenetic mark, the phosphorylation of the core histone variant H2AX (γH2AX). The very rapid local decondensation of chromatin, which occurs in a γH2AX-independent manner at DSB's can be attributed to poly(ADP-ribose) production that is mediated locally by PARP-1.

Also developmental or environmental cues, such as steroids or heat shock, induce PARP-1 activation and the poly (ADP-ribose)-dependent stripping of histones from chromatin, thereby favouring the opening of the chromatin structure, which may allow transcriptional activation in the absence of DNA breaks.

Extensive PARP activation in cells suffering from massive DNA damage leads to severe depletion of $NAD^+$. The short half-life of poly(ADP-ribose) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of $NAD^+$ to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to $NAD^+$ depletion due to poly(ADP-ribose) turnover. Thus, PARP or PARG inhibition is expected to preserve the cellular energy level thereby potentiating the survival of ischaemic tissues after insult.

As indicated above, the subcellular localization of several PARPs hints also to a physiological role of poly(ADP-ribosyl)ation in the regulation of cell division.

TANK-1 seems to be required for the polymerization of mitotic spindle-associated poly(ADP-ribose). The poly (ADP-ribosyl)ation activity of TANK-1 might be crucial for the accurate formation and maintenance of spindle bipolarity. Furthermore, PARP activity of TANK-1 has been shown to be required for normal telomere separation before anaphase. Interference with tankyrase PARP activity results in aberrant mitosis, which engenders a transient cell cycle arrest, probably due to spindle checkpoint activation, followed by cell death. Inhibition of tankyrases is therefore expected to have a cytotoxic effect on proliferating tumor cells.

PARP-1 and PARP-2 localize to centrosomes where they interact with kinetochore proteins. Ablation of the Parp-2 gene in mice causes significant DNA-damage-induced chromosome mis-segregation that is associated with kinetochore defects, which indicates that PARP-2 has a crucial guardian function in pericentric heterochromatin integrity. Furthermore PARP-1 associate with centrosomes linking the DNA-damage-surveillance network with the mitotic fidelity checkpoint.

The pivotal role of PARP in the repair of DNA strand breaks is well established, especially when caused directly by ionizing radiation or, indirectly after enzymatic repair of DNA lesions induced by methylating agents, topoisomerases I inhibitors and other chemotherapeutic agents as cisplatin and bleomycin. A variety of studies using "knockout" mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of the tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways.

U.S. Pat. No. 5,177,075 discusses several isoquinolines used for enhancing the lethal effects of ionizing radiation or chemotherapeutic agents on tumor cells. Weltin et al., ("Effect of 6(5-Phenanthridinone), an Inhibitor of Poly(ADP-ribose) Polymerase, on Cultured Tumor Cells", Oncol. Res., 6:9, 399-403 (1994)), discusses the inhibition of PARP activity, reduced proliferation of tumor cells, and a marked synergistic effect when tumor cells are co-treated with an alkylating drug.

Reviews of the state of the art has been published by Li and Zhang in IDrugs 2001, 4(7): 804-812, by Ame et al in Bioassays 2004, 26: 882-883 and by Nguewa et al., in Progress in Biophysic & Molecular Biology 2005, 88: 143-172.

Loss of PARP-1 increases the formation of DNA lesions that are repaired by homologous recombination without directly regulating the process of homologous recombination itself. Familial breast cancer is commonly associated with inherited defects in one of the BRCA1 or BRCA2 alleles. BRCA1 and BRCA2 are important for homologous recombination. The remaining functional BRCA1 or BRCA2 allele can be lost in some cells, thereby contributing to tumorigenisis. Thus, the tumors that arise are BRCA1 or BRCA2 deficient (e.g. $BRCA2^{-/-}$) whereas the somatic cells retain functional BRCA proteins ($BRCA2^{+/-}$). Inhibition of PARP activity in a BRCA1- or BRCA2-defective background might result in the generation of DNA lesions normally repaired by sister chromatid exchange, causing chromatid aberrations and loss of viability. Only relatively low levels of PARP-1 inhibitors may be required to produce a therapeutic effect given the acute sensitivity of the BRCA-defective cells. This is another example of a case where inhibitors of a normally non-essential DNA repair protein can be used as a single agent to treat tumors.

According to a review by Horvath and Szabo (Drug News Perspect 20(3), April 2007, 171-181) most recent studies demonstrated that PARP inhibitors enhance the cancer cell death primarily because they interfere with DNA repair on various levels. More recent studies have also demonstrated that PARP inhibitors inhibit angiogenesis, either by inhibiting growth factor expression, or by inhibiting growth factor-induced cellular proliferative responses. These findings might also have implications on the mode of PARP inhibitors' anticancer effects in vivo.

Also a study by Tentori et al. (Eur. J. Cancer, 2007, 43 (14) 2124-2133) shows that PARP inhibitors abrogate VEGF or placental growth factor-induced migration and prevent formation of tubule-like networks in cell-based systems, and impair angiogenesis in vivo. The study also demonstrates that growth factor-induced angiogenesis is deficient in PARP-1 knock-out mice. The results of the study provide evidence for targetting PARP for anti-angiogenesis, adding novel therapeutic implications to the use of PARP inhibitors in cancer treatment.

The PARP inhibitors of the present invention also demonstrate anticancer activity linked to disruption of tubulin polymerization.

Tubulin is composed of a heterodimer of two related proteins called $\alpha$ and $\beta$ tubulin. Tubulin polymerizes to form structures called microtubules. Microtubules are highly dynamic cytoskeletal elements and play a critical role in many processes in eukaryotic cells, including mitosis, cell mobility, cell shape, intracellular organelle transport and cell-cell interactions.

For proper cell division to occur, it is essential that microtubules are able to polymerize and depolymerize. Microtubules in the mitotic spindle are more dynamic than those in non-dividing cells, and thus can be targeted by agents that affect microtubule dynamics. By altering microtubule polymerization/depolymerization these agents affect mitotic spindle formation, arrest dividing cells in the G2/M phase of the cell cycle, and ultimately lead to apoptotic cell death. As neoplastic cells have high proliferation rates, they can be targeted by these antimitotic agents.

Three main classes of tubulin-binding drugs, namely colchicine analogues, Vinca alkaloids and the taxanes have been identified, each of which possesses a specific binding site on the $\beta$-tubulin molecules. Paclitaxel and related taxanes represent a class of drugs that stabilizes microtubules, a process that ultimately leads to the freezing of the microtubule structures so that they can not be restructured. Subsequent arrest at mitosis induces the apoptotic mechanism to cause cell death. The second class of compounds, the colchicine analogues, as well as several other compounds, bind to the same site on $\beta$-tubulin as colchicine and disrupt polymerization and microtubular formation. The third class of compounds, vinblastine and several other vinca-related drugs, bind to the Vinca-site and prevent microtubule formation and destabilize microtubules.

Tubulin is also a target for treating disease states that are dependent or result from the abnormal formation of blood vessels (neovascularisation) such as cancerous tumours. In these cases the cytoskeleton of the vascular endothelial cells are disrupted through depolymerization of microtubules, which results from inhibiting the polymerization of tubulin to form microtubules. Microtubule length is dependent on the rate of depolymerization versus polymerization. Depolymerising microtubules through inhibition of polymerization leads to a change in endothelial cell morphology, which than causes a blockage or shutdown in blood flow. In the case of cancerous tumours, blood flow to the diseased tissue is stopped, depriving the tumour from oxygen and nutrients leading to necrotic cell death. Neovascular systems are more sensitive to these agents because they are more dependent on microtubule cytoskeleton than normal, healthy vascular endothelial cells which are also supported by actin based cytoskeleton structures. For a number of tubulin polymerization inhibitors that target the colchicine binding site of tubulin, the vascular targeting modality can be achieved at a lower in vivo concentration than the antiproliferative modality. Thus, agents that target the colchicine binding domain of tubulin can be potentially dual mode agents i.e. antimitotic and antivascular.

There continues to be a need for effective and potent anticancer therapy that include efficacy against tumors that are currently untreatable or poorly treatable, efficacy against multi-drug resistant tumors and minimal side effects. The present invention provides compounds, compositions for, and methods of, inhibiting PARP activity and binding tubulin for treating cancer. The compounds and compositions of the present invention differ from the prior art in that they have a dual mode of action (PARP inhibition and tubulin binding). Furthermore they have a high TANK inhibitory activity resulting in enhanced anti-cancer effects making them in particular useful for single agent treatment. They are also useful in enhancing the effectiveness of chemotherapy and radiotherapy where a primary effect of the treatment with the compound is that of triggering cell death under conditions of DNA damage.

BACKGROUND PRIOR ART

WO03/101985, published on Dec. 11, 2003, discloses 2-oxo-1,3,4-trihydroquinazolinyl derivatives for the treatment of cell proliferation-related disorders.

EP 1487800, published on Oct. 2, 2005, discloses phenanthridinone as poly(ADP-ribose) polymerase inhibitors.

EP 1687277, published on Jun. 16, 2005, discloses 6-alkenyl and 6-phenylalkyl substituted 2-quinolinones and 2-quinoxalinones as poly(ADP-ribose) polymerase inhibitors.

EP 1709011, published on Jun. 16, 2005, discloses 6-phenylalkyl substituted 2-quinolinones and 2-quinoxalinones as poly(ADP-ribose) polymerase inhibitors.

EP 1709012, published on Jun. 16, 2005, discloses 6-substituted 2-quinolinones and 2-quinoxalinones as poly(ADP-ribose) polymerase inhibitors.

EP 1694653, published on Jun. 30, 2005, discloses substituted 6-cyclohexylalkyl substituted 2-quinolinones and 2-quinoxalinones as poly(ADP-ribose) polymerase inhibitors.

WO 2005/097750, published on Oct. 2, 2005, discloses substituted pyridones as poly(ADP-ribose) polymerase inhibitors.

WO2005/117876, published on Dec. 15, 2005, discloses dual small molecule inhibitors of cancer and angiogenesis.

WO 2006/003146, published on Jan. 12, 2006, discloses quinazolinones derivatives as poly(ADP-ribose) polymerase inhibitors.

WO 2006/003147, published on Jan. 12, 2006, discloses phthalazine derivatives as poly(ADP-ribose) polymerase inhibitors.

WO 2006/003148, published on Jan. 12, 2006, discloses quinazolinedione derivatives as poly(ADP-ribose) polymerase inhibitors.

WO 2006/003150, published on Jan. 12, 2006, discloses substituted 2-alkyl quinazolinone derivatives as poly(ADP-ribose) polymerase inhibitors.

WO 2007/025009, published on Mar. 1, 2007, discloses indenoisoquinolinone analogs as poly(ADP-ribose) polymerase inhibitors.

WO 2007/095628, published on Aug. 23, 2007, discloses pyrazoloquinolinones as potent PARP inhibitors.

WO2008/107478, published on Sep. 12, 2008, discloses quinolinone derivatives as PARP and TANK inhibitors.

Tentori et al., European Journal of Cancer, vol. 43, no. 14, 2007, relates to poly(ADP-ribose)polymerase (PARP) inhibition or PARP-1 gene deletion which reduces angiogenesis.

DESCRIPTION OF THE INVENTION

This invention concerns compounds of formula (I)

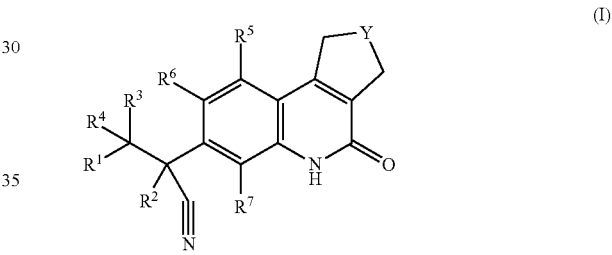

(I)

including the stereochemically isomeric forms thereof; wherein

Y is $CH_2$ or $CH_2$—$CH_2$, $R^1$ is aryl or Het;

wherein aryl is phenyl or naphthalenyl;

wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;

two carbon atoms on aryl or Het can be bridged (i.e. forming a bi- or tricyclic moiety) with a bivalent radical selected from —O—$CH_2$—$CH_2$—O— (a-1), —$CH_2$—O—$CH_2$—O— (a-2), —O—$CH_2$—$CH_2$—$CH_2$— (a-3), —O—$CH_2$—$CH_2$—$NR^8$— (a-4), —O—$CR^8_2$—O— (a-5), —O—CH₂—CH₂— (a-6), —CH₂—N—CH₂—CH₂— (a-7), —(CH₂)₃— (a-8), or —(CH₂)₄— (a-9);

each aryl, Het, bridged aryl or bridged Het can be substituted with one, two, three, four or five substituents each independently selected from halo, cyano, nitro, hydroxycarbonyl, $C_{1-6}$alkyl, $C_{2-6}$alkenyl, $C_{2-6}$alkynyl, $C_{3-6}$cycloalkyl, $C_{3-6}$cycloalkylamino, methylethylamino, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—CH₂O—CH₃, —C≡C—CH₂N(CH₃)₂, —C≡C—Si(CH₃)₃, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{2-6}$alkynyl, —PO(O$C_{1-6}$alkyl)₂, —B(OH)₂, —S—CH₃, SF₅, $C_{1-6}$alkylsulfonyl, —NR⁸R⁹, —$C_{1-6}$alkylNR⁸R⁹, —OR⁸, —$C_{1-6}$alkylOR⁸, —CONR⁸R⁹, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl; or $R^1$ is a radical of formula

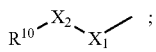    (b-1)

wherein $X_1$ is CH₂, NH or N—CH₃;
wherein $X_2$ is CH₂, C═O, O, NH or N—CH₃;
wherein $R^{10}$ is phenyl, pyridinyl, pyridazinyl or pyrimidinyl, wherein each phenyl, pyridinyl, pyridazinyl or pyrimidinyl can be substituted with one or two substituents each independently selected from halo, hydroxy, cyano, $C_{1-6}$alkyl, amino, polyhalo$C_{1-6}$alkyl or $C_{1-6}$alkyloxy; or $R^1$ is a radical of formula

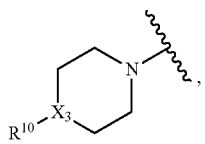    (b-2)

wherein $X_3$ is CH or N;
$R^2$ is methyl, ethyl, propyl or $C_{3-6}$cycloalkyl;
each $R^3$ and $R^4$ is independently selected from hydrogen, methyl, ethyl, propyl, hydroxy, trifluoromethyl, methyloxy; or $R^3$ and $R^4$ are taken together with the carbon atom to which they are attached to form a cyclopropyl ring or a radical of formula C(═O);

each $R^5$ and $R^6$ is independently selected from hydrogen, halo, $C_{1-6}$alkyloxy, cyano, $C_{1-6}$alkyl, —OCH₂CH₂NR⁸R⁹, —CH₂OCH₂CH₂NR⁸R⁹, —OCH₂CH₂CH₂NR⁸R⁹;

$R^7$ is hydrogen, methyl or fluor;

each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;

the N-oxide forms thereof, the pharmaceutically acceptable addition salts thereof and the solvates thereof.

The compounds of formula (I) and the intermediates of the invention may also exist in their tautomeric forms. Such forms although not explicitly indicated in the above formula are intended to be included within the scope of the present invention. The tautomeric forms of the compounds of formula (I) are meant to comprise those compounds of formula (I) wherein e.g. an enol group is converted into a keto group (keto-enol tautomerism).

Whenever the heterocyclic ring systems in $R^1$ contains a —CH₂—, —CH═, or —NH— moiety the substituents or the rest of the molecule can be attached to each carbon or nitrogen atom implying that one or both hydrogen atoms on the same carbon may be replaced.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; halo$C_{1-6}$alkyl defines $C_{1-6}$alkyl containing one halo substituent for example fluoromethyl; trihalo$C_{1-6}$alkyl defines $C_{1-6}$alkyl containing three identical or different halo substituents for example trifluoromethyl; polyhalo$C_{1-6}$alkyl as a group or part of a group is defined as $C_{1-6}$alkyl substituted with one or more, such as for example 2, 3, 4 or 5 halo atoms, for example methyl substituted with one or more fluoro atoms, for example, difluoromethyl or trifluoromethyl, 1,1-difluoro-ethyl, 1,1-difluoro-2,2,2-trifluoro-ethyl and the like. In case more than one halogen atoms are attached to a $C_{1-6}$alkyl group within the definition of polyhalo$C_{1-6}$alkyl, they may be the same or different; $C_{2-6}$alkenyl defines straight and branched chain hydrocarbon radicals containing a double bond, in particular one double bond, and having from 2 to 6 carbon atoms such as, for example, ethenyl, 2-propenyl, 3-butenyl, 2-pentenyl, 3-pentenyl, 3-methyl-2-butenyl, and the like; $C_{2-6}$alkynyl defines straight and branch chain hydrocarbon radicals containing a triple bond, in particular one triple bound, and having from 2 to 6 carbon atoms, such as, for example, ethynyl, 2-propynyl, 3-butynyl, 2-butynyl, 2-pentynyl, 3-pentynyl, 3-hexynyl, and the like; $C_{3-6}$cycloalkyl includes cyclic hydrocarbon groups having from 3 to 6 carbons, such as cyclopropyl, cyclobutyl, cyclopentyl, cyclohexyl, and the like.

The term "pharmaceutically acceptable addition salts" means pharmaceutically acceptable acid or base addition salts. The pharmaceutically acceptable acid or base addition salts as mentioned hereinabove or hereinafter are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

A quaternary ammonium salt of a compound according to formula (I) defines said compound which is able to form by a reaction between a basic nitrogen of a compound according to formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has at least one positively charged nitrogen. Pharmaceutically acceptable counterions include chloro, bromo, iodo, trifluoroacetate and acetate ions. The quaternary ammonium salts of the compounds of formula (I) are included within the ambit of the present invention.

The terms solvates comprise the hydrates and the solvent addition forms which the compounds of formula (I) are able to form and the pharmaceutically acceptable addition salts thereof. Examples of such forms are e.g. hydrates, alcoholates and the like.

The term stereochemically isomeric forms of compounds of formula (I), as used hereinbefore or hereinafter, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereochemically pure.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

If a compound is bearing one chiral centre and the two enantiomers of this compound have been separated, an asterix "*" in the drawing indicates that the absolute stereochemistry of the enantiomer has not been determined.

The N-oxide forms of the compounds of formula (I) are meant to comprise those compounds of formula (I) wherein one or several tertiary nitrogen atoms are oxidized to the so-called N-oxide, particularly those N-oxides wherein one or more of the piperidine- or piperazine nitrogens are N-oxidized.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" is meant to include also the N-oxide forms, the pharmaceutically acceptable acid or base addition salts, the solvates and all stereoisomeric forms thereof.

A first group of interesting compounds consists of those compounds of formula (I) wherein one or more of the following restrictions apply:
a) Y is $CH_2—CH_2$;
b) aryl is phenyl;
c) Het is pyridinyl, pyrimidinyl, benzimidazolyl or indazolyl;
d) each aryl or Het can be substituted with one or two substituents each independently selected from halo, cyano, $C_{1-6}$alkyl, $C_{1-6}$alkyloxycarbonyl, $C_{1-6}$alkyl$NR^8R^9$ or $—OR^8$;
e) $X_1$ is $CH_2$ or $N—CH_3$;
f) $X_2$ is $CH_2$, $C=O$ or $O$;
g) $R^{10}$ is phenyl which can be substituted with cyano;
h) $R^2$ is methyl;

j) $R^3$ and $R^4$ are hydrogen;

k) $R^5$ and $R^6$ are hydrogen;

l) $R^7$ is hydrogen; or m) each $R^8$ and $R^9$ is independently selected from hydrogen, halo, $C_{1-6}$alkyl or trihalo$C_{1-6}$alkyl.

A second group of interesting compounds consists of those compounds of formula (I) wherein $R^1$ is pyridinyl or pyrimidinyl.

A third group of interesting compounds consists of those compounds of formula (I) or of one of the above groups of interesting compounds of formula (I) wherein one or more of the following restrictions apply:

a) Y is $CH_2$—$CH_2$;

b) $R^1$ is phenyl, pyridinyl or pyrimidinyl;

c) each phenyl, pyridinyl or pyrimidinyl can be substituted with one or two substituents each independently selected from halo, cyano or $C_{1-6}$alkyloxy;

e) $X_1$ is $CH_2$;

f) $X_2$ is O;

g) $R^{10}$ is phenyl substituted with cyano;

d) $R^2$ is methyl;

e) $R^3$ and $R^4$ are hydrogen;

h) $R^5$ and $R^6$ are hydrogen; or i) $R^7$ is hydrogen.

A group of preferred compounds consists of those compounds of formula (I) wherein Y is $CH_2$—$CH_2$; aryl is phenyl; Het is pyridinyl, pyrimidinyl, benzimidazolyl or indazolyl; each aryl or Het can be substituted with one or two substituents each independently selected from halo, cyano, $C_{1-6}$alkyl, $C_{1-6}$alkyloxycarbonyl, —$C_{1-6}$alkylNR$^8$R$^9$ or —OR$^8$; $X_1$ is $CH_2$ or N—$CH_3$; $X_2$ is $CH_2$, C=O or O; $R^{10}$ is phenyl which can be substituted with cyano; $R^2$ is methyl; $R^3$ and $R^4$ are hydrogen; $R^5$ and $R^6$ are hydrogen; $R^7$ is hydrogen; and each $R^8$ and $R^9$ is independently selected from hydrogen, halo, $C_{1-6}$alkyl or trihalo$C_{1-6}$alkyl.

A group of more preferred compounds consists of those compounds of formula (I) wherein Y is $CH_2$—$CH_2$; $R^1$ is phenyl, pyridinyl or pyrimidinyl; each phenyl, pyridinyl or pyrimidinyl can be substituted with one or two substituents each independently selected from halo, cyano or $C_{1-6}$alkyloxy; $X_1$ is $CH_2$; $X_2$ is O; $R^{10}$ is phenyl substituted with cyano; $R^2$ is methyl; $R^3$ and $R^4$ are hydrogen; $R^5$ and $R^6$ are hydrogen; and $R^7$ is hydrogen.

The most preferred compounds are Co. No. 6, Co. No. 5b, Co. No. 7, Co. No. 4 and Co. No. 17.

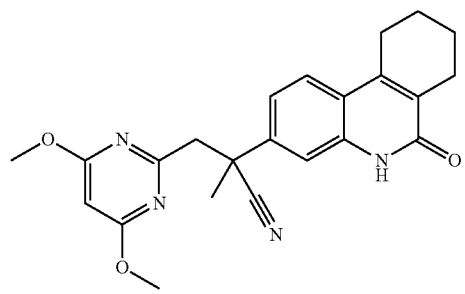

Co. No. 6

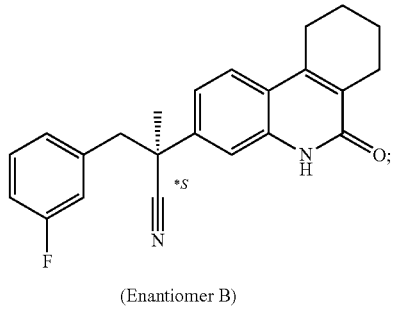

Co. No. 5b (Enantiomer B)

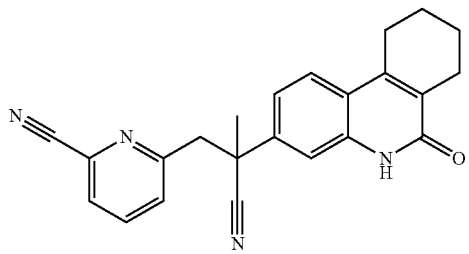

Co. No. 7

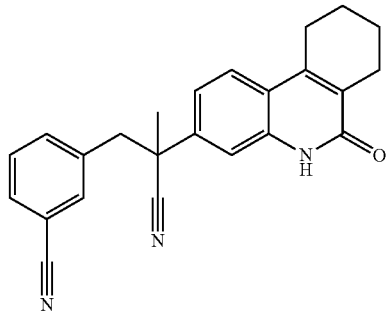

Co. No. 4

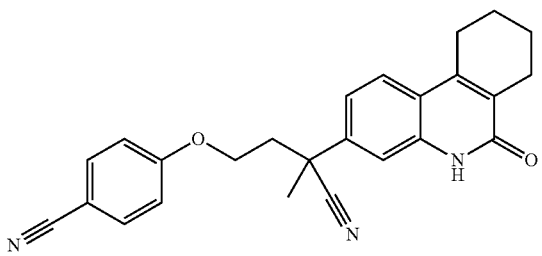

Co. No. 17 and the N-oxide forms thereof, the pharmaceutically acceptable addition salts thereof and the solvates thereof; in particular and the pharmaceutically acceptable addition salts thereof and the solvates thereof; more in particular and the pharmaceutically acceptable addition salts thereof.

The compounds of formula (I) can be prepared according to the general methods described herein below. The starting materials and some of the intermediates are known compounds and are commercially available or may be prepared according to conventional reaction procedures generally known in the art.

Some preparation methods will be described hereinafter in more detail. Other methods for obtaining final compounds of formula (I) are described in the examples.

Compounds of formula (I) can be prepared by hydrolysing intermediates of formula (II), according to art-known methods, by submitting the intermediates of formula (II) to appropriate reagents, such as hydrochloric acid, in the presence of a reaction inert solvent, such as dioxane.

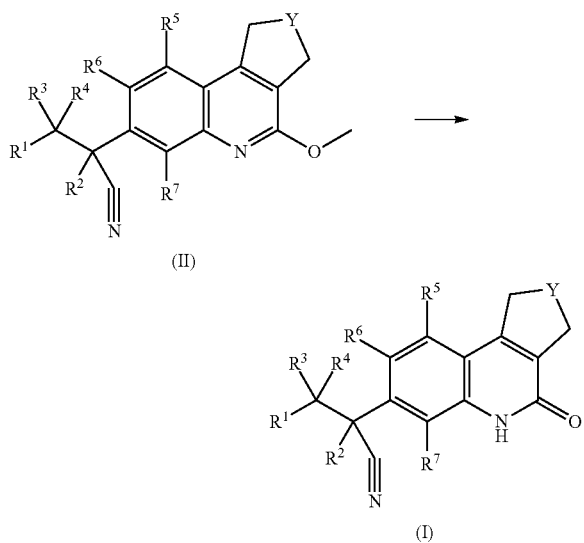

Alternatively, compounds of formula (I) can be prepared by adding an excess of a base, for example 2-methyl-2-propanol, potassium salt or lithium diisopropylamide to intermediates of formula (III) in the presence of intermediates of formula (IV), wherein Halo is chloro or bromo, in a suitable solvent such as tetrahydrofuran, dioxane or dimethylformamide.

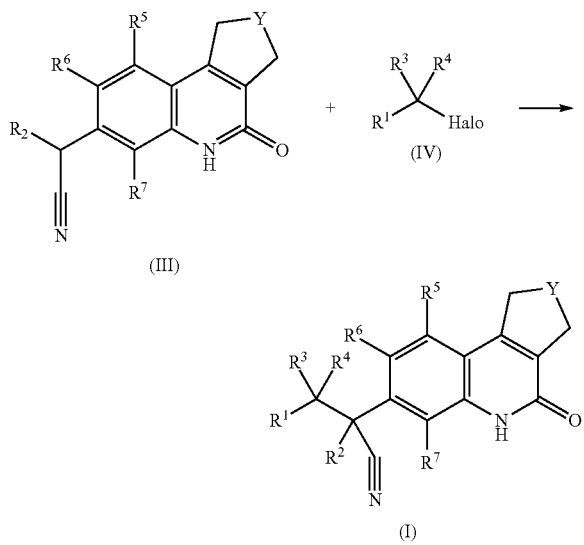

The present invention also concerns the intermediates of formula (II)

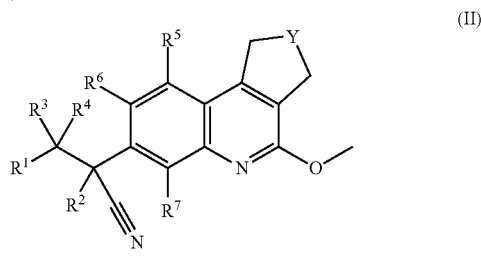

including the stereochemically isomeric forms thereof;

wherein
Y is $CH_2$ or $CH_2$—$CH_2$,
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged (i.e. forming a bi- or tricyclic moiety) with a bivalent radical selected from

| | |
|---|---|
| —O—$CH_2$—$CH_2$—O— | (a-1), |
| —$CH_2$—O—$CH_2$—O— | (a-2), |
| —O—$CH_2$—$CH_2$—$CH_2$— | (a-3), |
| —O—$CH_2$—$CH_2$—$NR^8$— | (a-4), |
| —O—$CR^8{}_2$—O— | (a-5), |
| —O—$CH_2$—$CH_2$— | (a-6), |
| —$CH_2$—N—$CH_2$—$CH_2$— | (a-7), |
| —$(CH_2)_3$— | (a-8), | or

| | |
|---|---|
| —$(CH_2)_4$— | (a-9); | each aryl, Het, bridged aryl or bridged Het can be substituted with one, two, three, four or five substituents each independently selected from halo, cyano, nitro, hydroxycarbonyl, $C_{1-6}$alkyl, $C_{2-6}$alkenyl, $C_{2-6}$alkynyl, $C_{3-6}$cycloalkyl, $C_{3-6}$cycloalkylamino, methylethylamino, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—$CH_2$O—$CH_3$, —C≡C—$CH_2$N$(CH_3)_2$, —C≡C—Si$(CH_3)_3$, hydroxy $C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl-$C_{1-6}$alkyl, $C_{1-6}$alkylsulfonyl$C_{2-6}$alkenyl, $C_{1-6}$alkylsulfonyl$C_{2-6}$alkynyl, —PO(O$C_{1-6}$alkyl)$_2$, —B(OH)$_2$, —S—$CH_3$, $SF_5$, $C_{1-6}$alkylsulfonyl, —$NR^8R^9$, —$C_{1-6}$alkylN$R^8R^9$, —$OR^8$, —$C_{1-6}$alkylO$R^8$, —CON$R^8R^9$, piperidinyl$C_{1-6}$alkyl, piperazinyl$C_{1-6}$alkyl, $C_{1-6}$alkyl-piperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl; or
$R^1$ is a radical of formula

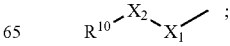

(b-1)

wherein $X_1$ is $CH_2$, NH or N—$CH_3$;

wherein $X_2$ is $CH_2$, C=O, O, NH or N—$CH_3$;

wherein $R^{10}$ is phenyl, pyridinyl, pyridazinyl or pyrimidinyl, wherein each phenyl, pyridinyl, pyridazinyl or pyrimidinyl can be substituted with one or two substituents each independently selected from halo, hydroxy, cyano, $C_{1-6}$alkyl, amino, polyhalo$C_{1-6}$alkyl or $C_{1-6}$alkyloxy; or $R^1$ is a radical of formula

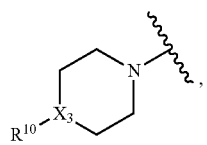

(b-2)

wherein $X_3$ is CH or N;

$R^2$ is methyl, ethyl, propyl or $C_{3-6}$cycloalkyl;

each $R^3$ and $R^4$ is independently selected from hydrogen, methyl, ethyl, propyl, hydroxy, trifluoromethyl, methyloxy; or $R^3$ and $R^4$ are taken together with the carbon atom to which they are attached to form a cyclopropyl ring or a radical of formula C(=O);

each $R^5$ and $R^6$ is independently selected from hydrogen, halo, $C_{1-6}$alkyloxy, cyano, $C_{1-6}$alkyl, —OCH$_2$CH$_2$NR$^8$R$^9$, —CH$_2$OCH$_2$CH$_2$NR$^8$R$^9$, —OCH$_2$CH$_2$CH$_2$NR$^8$R$^9$;

$R^7$ is hydrogen, methyl or fluor;

each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino $C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl $C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl $C_{1-6}$alkyl or $C_{1-6}$alkylcarbonylamino$C_{1-6}$alkyl;

the N-oxide forms thereof, the pharmaceutically acceptable addition salts thereof and the solvates thereof.

Groups of interesting, preferred, more preferred and most preferred compounds can be defined for the compounds of formula (II), in accordance with the groups defined for the compounds of formula (I).

Intermediates of formula (II) can be prepared by adding 2-methyl-2-propanol, potassium salt to intermediates of formula (V) in the presence of intermediates of formula (VI), wherein W is a leaving group such as chloro, bromo or mesylate, in a suitable solvent such as tetrahydrofuran.

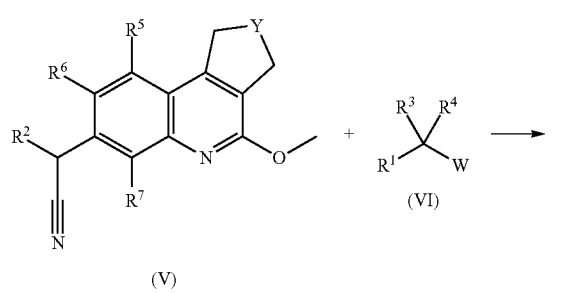

(V)

(VI)

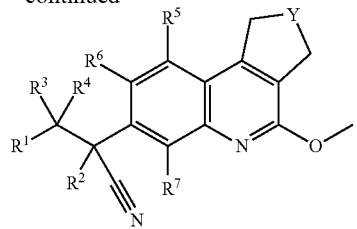

(II)

Intermediates of formula (III) can be prepared by submitting the intermediates of formula (V) to appropriate reagents, such as hydrochloric acid, in the presence of a reaction inert solvent, e.g. dioxane.

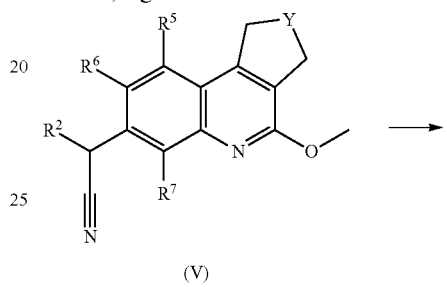

(V)

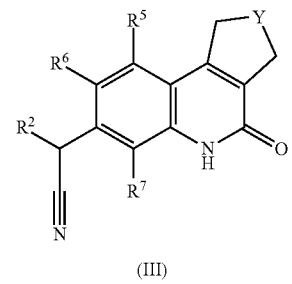

(III)

Intermediates of formula (V) can be prepared by adding a mixture of 2-methyl-2-propanol, potassium salt and tosylmethyl isocyanide in dimethylsulfoxide to an intermediate of formula (VIII) in a suitable solvent such as methanol.

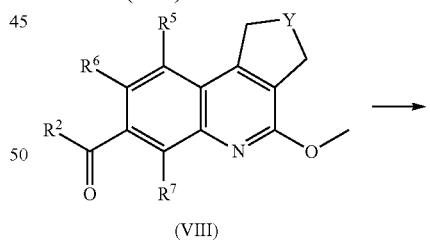

(VIII)

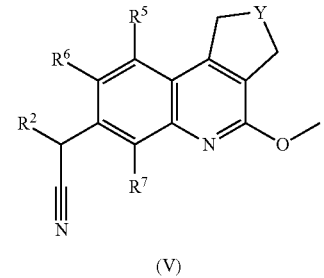

(V)

Intermediates of formula (VIII) can be prepared by treating an intermediate of formula (IX), with an organolithium reagent such as, e.g. n-butyllithium in a reaction inert solvent, e.g. tetrahydrofuran, and subsequently reacting said intermediate with an intermediate of formula (X).

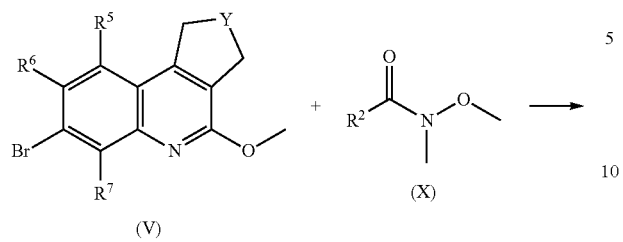

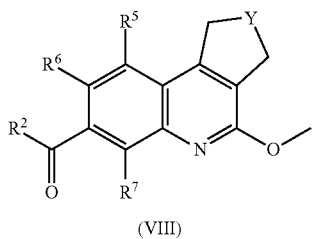

Intermediates of formula (VIII) can also be prepared by converting intermediates of formula (XI) in the presence of a suitable oxidant such as manganese dioxide in a suitable solvent such as dioxane or in the presence of potassium manganese tetraoxide and Tris[2-(2-methoxyethoxy)ethyl]amine, in a suitable solvent such as dichloromethane.

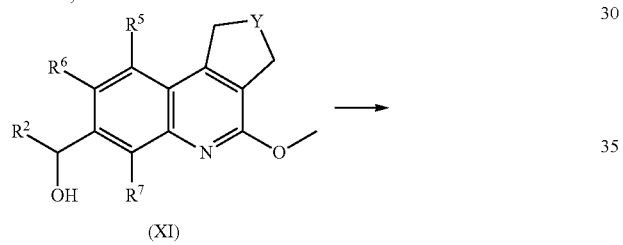

Intermediates of formula (XI) can be prepared by treating an intermediate of formula (IX), with an organolithium reagent such as, e.g. n-butyllithium, in a reaction inert solvent, e.g. tetrahydrofuran, and subsequently reacting said intermediate with an intermediate of formula (XII).

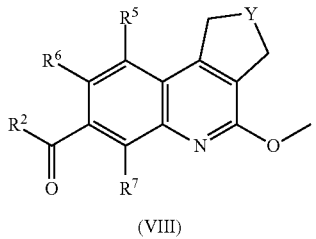

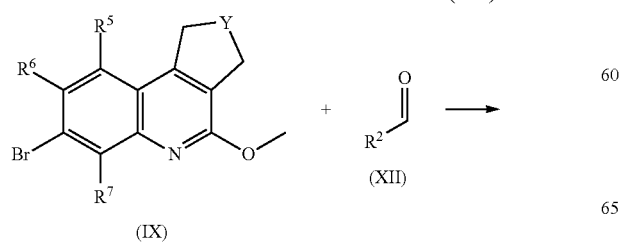

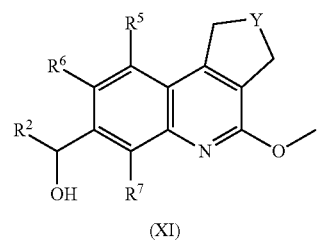

Intermediates of formula (IX) can be prepared by adding methanol sodium salt in methanol, to intermediates of formula (XIII), wherein Halo means independently chloro or bromo, in a suitable solvent such as methanol.

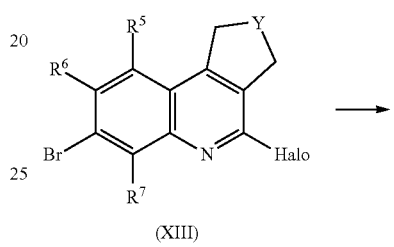

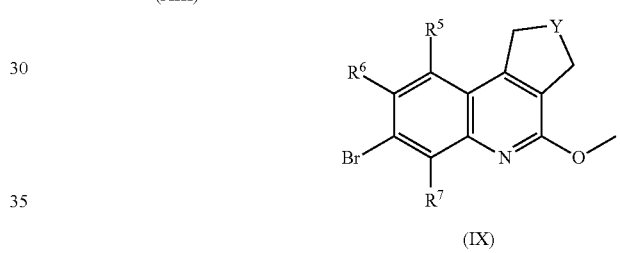

Intermediates of formula (XIII) can be prepared by reacting intermediates of formula (XIV) with a suitable halogenating agent for example phosphorus oxychloride, at a suitable temperature, preferentially at reflux.

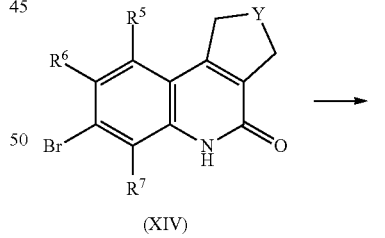

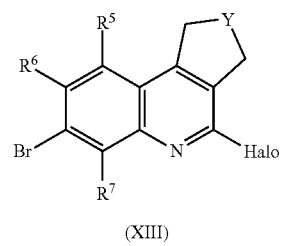

Intermediates of formula (XIV) can be prepared by heating intermediates of formula (XV), in an acidic medium, preferentially in sulfuric acid.

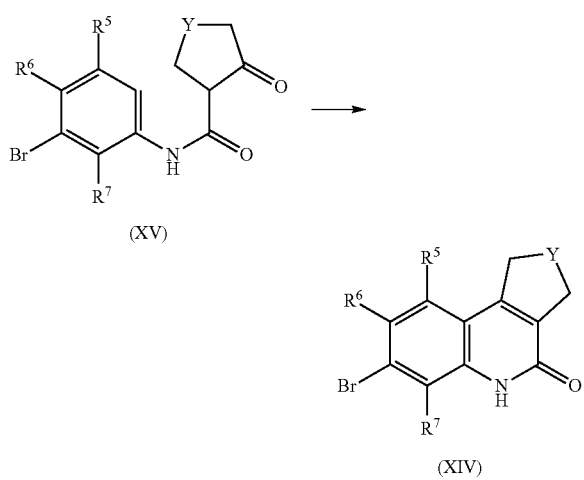

The compounds of formula (I) or their intermediates may also be converted into each other via art-known reactions or functional group transformations. Some of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted into an ester group by carbon monoxide insertion in the presence of a suitable palladium catalyst; an iodo radical on a phenyl group may be converted into a $C_{2-6}$alkynyl group or a derivative thereof (e.g —C≡C—Si($CH_3$)$_3$ or hydroxy$C_{2-6}$alkynyl) by reaction with the suitable $C_{2-6}$alkynyl compound or derivative thereof in the presence of a suitable palladium catalyst; a —C≡C—Si($CH_3$)$_3$ radical on a phenyl group may be converted into —C≡CH in the presence of a suitable base.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The present invention also relates to a compound of formula (I) as defined above for use as a medicine; in particular for use in the treatment of a tubulin polymerization mediated disorder, a PARP mediated disorder or a TANK mediated disorder, for use to inhibit tumour growth, for use to inhibit abnormal growth of cells.

The compounds of the present invention have PARP inhibiting and tubulin polymerization inhibiting properties as can be seen from the experimental part hereinunder.

The term "PARP" is used herein to mean a protein having poly-ADP-ribosylation activity. Within the meaning of this term, PARP encompasses all proteins encoded by a parp gene, mutants thereof, and alternatively spliced proteins thereof. Additionally, as used herein, the term "PARP" includes PARP analogues, homologues and orthologues in other animals.

The term "PARP", includes but is not limited to PARP-1. Within the meaning of this term PARP-2, PARP-3, Vault-PARP (PARP-4), PARP-7 (TiPARP), PARP-8, PARP-9 (Ba1), PARP-10, PARP-11, PARP-12, PARP-13, PARP-14, PARP-15, PARP-16, TANK-1, TANK-2, and TANK-3 may be encompassed.

The term "PARP inhibitor" or "inhibitor of PARP" is used to identify a compound, which is capable of interacting with a PARP or a TANK and inhibiting its activity, more particularly its enzymatic activity. Inhibiting PARP or TANK enzymatic activity means reducing the ability of a PARP or a TANK to produce poly(ADP-ribose) or to induce poly(ADP-ribosyl)ation of a substrate. Preferably, such inhibition is specific, i.e. the PARP inhibitor reduces the ability of a PARP to produce poly(ADP-ribose) or to induce poly(ADP-ribosyl)ation of a substrate at a concentration that is lower than the concentration of the inhibitor that is required to produce some other, unrelated biological effect.

The term "compound with tubulin polymerization inhibiting properties" or "tubulin polymerization inhibitor" is used to identify a compound that
  stabilize microtubules, inhibit the depolymerization of microtubules, stabilizes the microtubules or freeze the microtubular structure,
  disrupt polymerization of microtubules and disrupt microtubular formation, or
  destabilize microtubules and prevent microtubule formation.

The compounds of the present invention are TANK specific PARP inhibitors. The term "TANK specific PARP inhibitors" is used to identify compounds which reduce the enzymatic activity of a TANK member (e.g. TANK-2) at a concentration that is lower than the concentration of the inhibitor that is required to produce inhibition of another PARP enzyme such as e.g. PARP-1.

The present invention also contemplates the use of compounds in the preparation of a medicament for the treatment of any of the diseases and disorders in an animal, particularly a human, described herein.

The present invention also contemplates the use of compounds of formula (I) for the manufacture of a medicament for the treatment of a PARP, a TANK or a tubulin polymerization mediated disorder.

In view of their PARP binding properties, the compounds of the present invention may be used as reference compounds or tracer compounds in which case one of the atoms of the molecule may be replaced with, for instance, a radioactive isotope.

The present invention also comprises a pharmaceutical composition comprising a pharmaceutically acceptable carrier and as an active ingredient a therapeutically effective amount of a compound of the present invention.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging, to extend the lifespan and proliferative capacity of cells; to alter gene expression of senescent cells; chemosensitize and/or radiosensitize (hypoxic) tumor cells. The present invention also relates to treating diseases and conditions in an animal, in particular a human, which comprises administering to said animal a therapeutically effective amount of the above-identified compounds.

In particular, the present invention relates to a method of treating, preventing or inhibiting a neurological disorder in an animal, which comprises administering to said animal, in particular a human, a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

The present invention also contemplates the use of compounds of formula (I) for inhibiting PARP activity, for treating, preventing or inhibiting tissue damage resulting from cell damage or death due to necrosis or apoptosis, for treating, preventing or inhibiting a neurological disorder in an animal.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition. Preferably, the term "treatment" means (ii) or (iii).

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation. Diseases which are treatable with ionizing radiation include neoplastic diseases, benign and malignant tumors, and cancerous cells. Ionizing radiation treatment of other diseases not listed herein are also contemplated by the present invention.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics. Diseases which are treatable with chemotherapy include neoplastic diseases, benign and malignant tumors and cancerous cells. Chemotherapy treatment of other diseases not listed herein are also contemplated by the present invention.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

The compounds, compositions and methods of the present invention are particularly useful for treating or preventing tissue damage resulting from cell death or damage due to necrosis or apoptosis.

The compounds of the present invention can be "anticancer agents", which term also encompasses "anti-tumor cell growth agents" and "anti-neoplastic agents".

This invention also provides a method for inhibiting tumour growth by administering an effective amount of a compound of the present invention, to a subject, e.g. a mammal (and more particularly a human) in need of such treatment.

For example, the methods of the invention are useful for treating cancers and chemosensitizing and/or radiosensitizing tumor cells in cancers.

Examples of tumours, including adult and pediatric malignancies, which may be inhibited by the compounds of the present invention include, but are not limited to, lung cancer including small cell lung cancer and non-small cell lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemias (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcomas, liposarcomas, gastrointestinal stromal sarcomas, malignant peripheral nerve sheath tumours (MPNST), Ewing sarcomas, leiomyosarcomas, mesenchymal chondrosarcomas, lymphosarcomas, fibrosarcomas, rhabdomyosarcomas, melanomas, teratocarcinomas, neuroblastomas, brain tumours, medulloblastoma, gliomas, benign tumour of the skin (e.g. keratoacanthomas), breast carcinoma (e.g. advanced breast cancer), kidney carcinoma, nephroblastoma, ovary carcinoma, cervical carcinoma, endometrial carcinoma, bladder carcinoma, prostate cancer including the advanced disease and hormone refractory prostate cancer, testicular cancers, osteosarcoma, head and neck cancer, epidermal carcinoma, multiple myeloma (e.g. refractory multiple myeloma), mesothelioma. Particular cancers that can be treated with the compounds of the present invention are breast cancer, colorectal cancer, non-small cell lung cancer, acute myelogenous leukemia (AML).

As another aspect of the present invention, a combination of a PARP inhibitor or a compound with tubulin binding properties of formula (I) with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoïden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrozole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, caminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitertinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

The term "platinum coordination compound" is used herein to denote any tumour cell growth inhibiting platinum coordination compound which provides platinum in the form of an ion. The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The term "taxane compounds" indicates a class of compounds having the taxane ring system and related to or derived from extracts from certain species of yew (Taxus) trees. The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The term "topoisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree *Nothapodytes foetida*. The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The term "podophyllotoxin compounds" is used to indicate compounds that are related to or derived from the parent podophyllotoxin, which is extracted from the mandrake plant. The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The term "anti-tumour vinca alkaloids" is used to indicate compounds that are related to or derived from extracts of the periwinkle plant (*Vinca rosea*). The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties. The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The term "anti-tumour anthracycline derivatives" comprise antibiotics obtained from the fungus *Strep. peuticus* var. *caesius* and their derivatives, characterised by having a tetracycline ring structure with an unusual sugar, daunosamine, attached by a glycosidic linkage. The anti-tumour anthracycline derivative is advantageously administered in a dosage of 10 to 75 mg per square meter (mg/m$^2$) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to identify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

The compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease. Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5' deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumor or other therapeutically effective compounds for treating cancer or other disease.

The compounds of formula (I) can also be used to detect or identify the PARP, and more in particular the PARP-1 receptor or the tankyrase receptor. For that purpose the compounds of formula (I) can be labeled. Said label can be selected from the group consisting of a radioisotope, spin label, antigen label, enzyme label fluorescent group or a chemiluminiscent group.

The present invention also relates to a combination according to the invention for use in medical therapy for example for inhibiting the growth of tumour cells.

The present invention also relates to a combination according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and the PARP inhibitor with tubulin binding properties may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and PARP inhibitor being administered, their route of administration, the particular tumour being treated and the particular host being treated. The optimum method and order of administration and the dosage amounts and regime can be readily determined by those skilled in the art using conventional methods and in view of the information set out herein.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the active ingredient, and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXPERIMENTAL PART

Hereinafter, "DMF" is defined as N,N-dimethylformamide, "DCM" is defined as dichloromethane, "DIPE" is defined as diisopropylether, "DMSO" is defined as dimethylsulfoxide, "EtOAc" is defined as ethyl acetate, "MeOH" is defined as methanol, "THF" is defined as tetrahydrofuran.

Of some compounds having 1 chiral center the absolute stereochemical configuration of the stereogenic carbon atom therein was not experimentally determined. In those cases the stereochemically isomeric form which was first isolated is designated as "enantiomer A" and the second as "enantiomer B", without further reference to the actual stereochemical configuration. However, said actual stereochemical configuration of "enantiomer A" and "enantiomer B" forms can unambiguously be characterized by a person skilled in the art, using art-known methods such as, for example, X-ray diffraction. The isolation method is described in detail below.

A. Preparation of the Intermediates

Example A1 a) Preparation of Intermediate 1

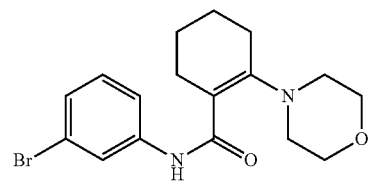 [SMILES: O=C(Nc1cccc(Br)c1)C1=C(N2CCOCC2)CCCC1]

A solution of 4-cyclohex-1-enyl-morpholine (0.0265 mol) in DCM (25 mL) was added dropwise at room temperature to a solution of 1-bromo-3-isocyanatobenzene (0.0252 mol) in DCM (30 mL). The mixture was stirred at room temperature for 15 hours and evaporated to dryness, yielding 11 g (91%) of intermediate 1, which was used without further purification in the next reaction step.

b) Preparation of Intermediate 2

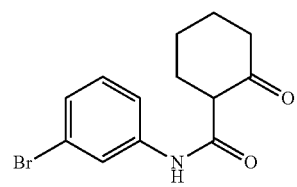 [SMILES: O=C1CCCCC1C(=O)Nc1cccc(Br)c1]

A solution of intermediate 1 (0.0252 mol) in concentrated sulfuric acid (40 mL) was stirred at 100° C. for 30 minutes, then cooled to room temperature, poured out into ice water and stirred again at room temperature for 1 hour and 30 minutes. The precipitate was filtered, washed with water, diethyl ether and dried, yielding 8.4 g of intermediate 2.

c) Preparation of Intermediate 3

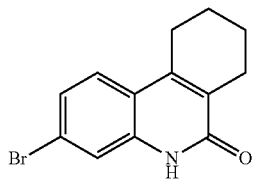

A solution of intermediate 2 (0.0017 mol) in 96% sulfuric acid (2 mL) was stirred at 100° C. for 15 minutes, then poured out into ice water with caution, filtered, washed twice with water and dried, yielding 0.441 g (93%) of intermediate 3 which was used without further purification in the next reaction step.

d) Preparation of Intermediate 4a

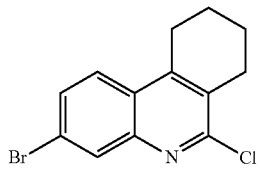 [SMILES: Clc1nc2cc(Br)ccc2c2c1CCCC2]

A solution of intermediate 3 (0.023 mol) in phosphorus oxychloride (100 mL) was stirred and refluxed till complete dissolution, left ten minutes, cooled to room temperature, poured out into water at room temperature very slowly (over one hour) under vigorous stirring. The solid was filtered off and dried, yielding 5.07 g (74%) of intermediate 4a, melting point: 84° C.

e) Preparation of Intermediate 4

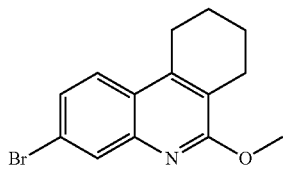 [SMILES: COc1nc2cc(Br)ccc2c2c1CCCC2]

A solution of sodium methoxide (0.101 mol) was added to a solution of intermediate 4a (0.0253 mol) in methanol (100 mL) at room temperature. The resulting mixture was stirred and refluxed for 15 hours, cooled to room temperature and poured out into water. The mixture was extracted with DCM, the organic layer was separated, washed with water, dried (MgSO$_4$), filtered and the solvent was evaporated to dryness, yielding 6.1 g (83%) of intermediate 4.

f) Preparation of Intermediate 5

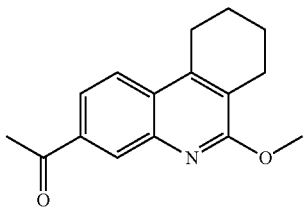 [SMILES: COc1nc2cc(C(C)=O)ccc2c2c1CCCC2]

Tributyl(1-ethoxyvinyl)tin (0.018 mol) then dichlorobis(triphenylphosphine)-palladium(II) (0.0008 mol) were added to a solution of intermediate 4 (0.016 mol) in dry toluene (29 mL) under inert atmosphere. The mixture was stirred and heated at 80° C. for 18 hours, cooled to room temperature and filtered over celite. The organic layer was washed with HCl 2M, then with brine till pH was set to 7, dried (MgSO$_4$), filtered and the solvent was evaporated under reduced pressure. The residue was purified by column chromatography over silica gel (eluent: cyclohexane/EtOAc from 95/5 to 80/20). The pure fractions were collected and the solvent was evaporated, yielding 1.3 g (31%) of intermediate 5.

g) Preparation of Intermediate 6

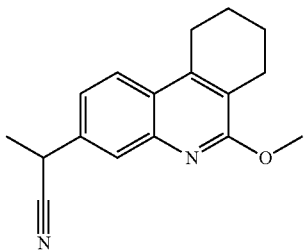 [SMILES: COc1nc2cc(C(C)C#N)ccc2c2c1CCCC2]

Potassium; 2-methyl-propan-2-olate (0.023 mol) then MeOH (2.4 mL) were added portionwise at 10° C. to a solution of p-toluenesulfonylmethylisocyanide (0.012 mol) in DMSO (12 mL) under N$_2$ flow. The mixture was stirred at 10° C. for 15 minutes. A solution of intermediate 5 (0.0051 mol) in DMSO (1.3 mL) was added. The mixture was stirred at 10° C. for 1 hour and 15 minutes and extracted with DCM and EtOAc. The organic layer was separated, dried (MgSO$_4$), filtered and the solvent was evaporated under reduced pressure. The residue was purified by column chromatography over silica gel (eluent: petroleum ether/EtOAc from 90/10 to 50/50). The pure fractions were collected and the solvent was evaporated, yielding 0.923 g (38%) of intermediate 6 (oil).

h) Preparation of Intermediate 7

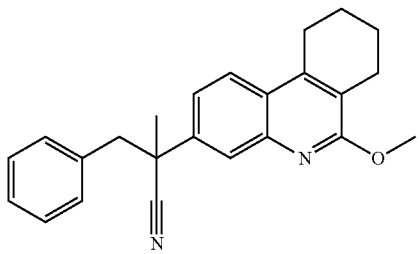 [SMILES: COc1nc2cc(C(C)(C#N)Cc3ccccc3)ccc2c2c1CCCC2]

Sodium hydride (60% dispersion in oil) (0.0005 mol) was added slowly at 0° C. to a solution of intermediate 6 (0.0003 mol) in DMF (1.4 mL) under $N_2$ flow. The mixture was stirred for 5 minutes. Bromomethyl-benzene (0.0005 mol) was added. The mixture was stirred at room temperature for 18 hours. Sodium hydride (0.0005 mol) was added again. The mixture was stirred for 3 hours, quenched with saturated ammonium chloride and extracted with EtOAc. The organic layer was washed with brine, dried (MgSO$_4$), filtered and the solvent was evaporated under reduced pressure. The residue was purified by column chromatography over silica gel (eluent: petroleum ether/EtOAc from 95/5 to 90/10). The pure fractions were collected and the solvent was evaporated, yielding 0.159 g (99%) of intermediate 7.

i) Preparation of Intermediate 7a and 7b

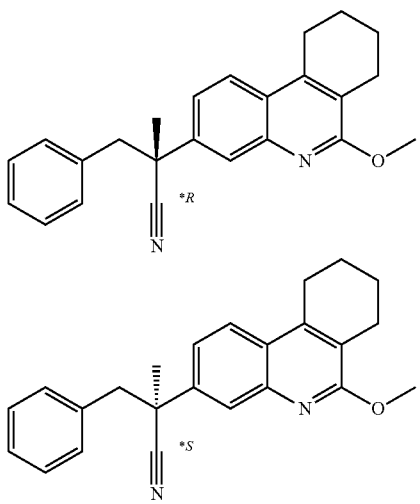

Intermediate 7 (0.28 g, 0.0008 mol) was separated into its enantiomers by superfluid chromatography on chiral silica gel (column Chiralpak®, eluent: CO$_2$/EtOH/iPrOH/isopropylamine: 70/15/15/0.3). The pure fractions were collected and the solvent was evaporated to give 0.115 g (29%) of intermediate 7a (enantiomer A) and 0.120 g (30%) of intermediate 7b (enantiomer B).

Example A2

Preparation of Intermediate 8

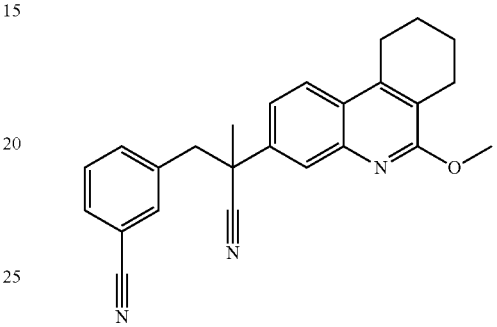

Sodium hydride (60% dispersion in oil) (0.0006 mol) was added portionwise at 0° C. to a solution of intermediate 6 (0.0004 mol) in DMF (1.7 mL) under $N_2$ flow. The mixture was stirred for 5 minutes. 3-Bromomethyl-benzonitrile (0.0006 mol) was added. The mixture was stirred at room temperature for 18 hours. Sodium hydride (0.0006 mol) was added again. The mixture was stirred for 3 hours, quenched with saturated ammonium chloride and extracted with EtOAc. The organic layer was washed with brine, dried (MgSO$_4$), filtered and the solvent was evaporated under reduced pressure. The residue was purified by column chromatography over silica gel (eluent: cyclohexane/EtOAc 80/20). The pure fractions were collected and the solvent was evaporated, yielding 0.0963 g (52%) of intermediate 8 (oil).

Example A3

Preparation of Intermediate 9

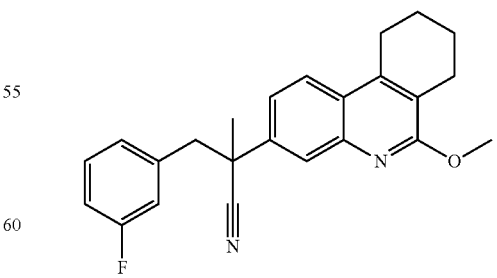

Potassium; 2-methyl-propan-2-olate (0.0011 mol) was added portionwise at 5° C. to a solution of intermediate 6 (0.0006 mol) and 1-bromomethyl-3-fluorobenzene (0.0008 mol) in THF (5 mL) under $N_2$ flow. The mixture was stirred at room temperature for 5 hours, poured out into ice water and extracted with EtOAc. The organic layer was separated, dried (MgSO₄), filtered and the solvent was evaporated. The residue was purified by column chromatography over silica gel (eluent: cyclohexane/EtOAc 95/5). The pure fractions were collected and the solvent was evaporated, yielding 0.33 g (78%) of intermediate 9.

Example A4

Preparation of Intermediate 10

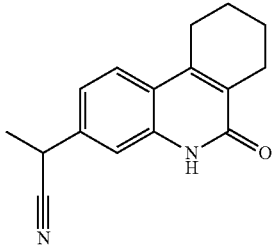 [SMILES: CC(C#N)c1ccc2c3c(c(=O)[nH]c2c1)CCCC3]

A mixture of intermediate 6 (0.0009 mol) in HCl 3N (2 mL) and 1,4-dioxane (2 mL) was stirred at 80° C. for 4 hours, then cooled to room temperature and basified with 10% K₂CO₃. The precipitate was filtered, washed with water, then with diethyl ether and dried, yielding 0.08 g (35%) of intermediate 10.

Example A5

Preparation of Intermediate 11

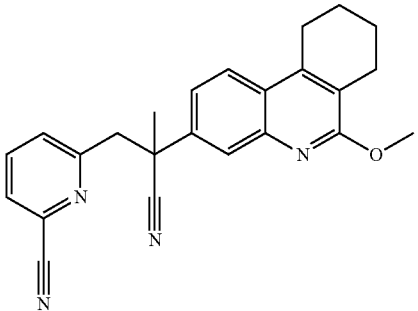 [SMILES: COc1nc2cc(C(C)(C#N)Cc3cccc(C#N)n3)ccc2c2c1CCCC2]

Potassium; 2-methyl-propan-2-olate (0.0015 mol) was added portionwise at 5° C. to a mixture of intermediate 6 (0.0007 mol) and 6-bromomethylpyridine-2-carbonitrile (0.0011 mol) in THF (5 mL) under N₂ flow. The mixture was stirred at room temperature for 5 hours, poured out into ice water and extracted with EtOAc. The organic layer was separated, dried (MgSO₄), filtered and the solvent was evaporated, yielding 0.25 g of intermediate 11 which was used without further purification in the next reaction step.

Example A6

Preparation of Intermediate 12

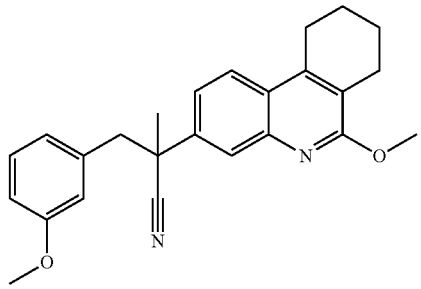 [SMILES: COc1cccc(CC(C)(C#N)c2ccc3c4c(c(OC)nc3c2)CCCC4)c1]

Potassium; 2-methyl-propan-2-olate (0.0011 mol) was added portionwise at 10° C. to a solution of intermediate 6 (0.00056 mol) and 1-bromomethyl-3-trifluoromethoxy-benzene (0.0008 mol) in THF (10 mL) under N₂ flow. The mixture was stirred at room temperature for 5 hours, poured out into ice water and extracted with EtOAc. The organic layer was separated, dried (MgSO₄), filtered and the solvent was evaporated to dryness, yielding 0.245 g (99%) of intermediate 12.

Example A7

Preparation of Intermediate 13

Potassium; 2-methyl-propan-2-olate (0.0011 mol) was added portionwise at 10° C. to a solution of intermediate 6 (0.0006 mol) and 1-bromomethyl-3-methoxy-benzene (0.0008 mol) in THF (5 mL) under N₂ flow. The mixture was stirred at room temperature for 5 hours, poured out into ice water and extracted with EtOAc. The organic layer was separated, dried (MgSO$_4$), filtered and the solvent was evaporated to dryness, yielding 0.215 g (99%) of intermediate 13.

Example A8

Preparation of Intermediate 14

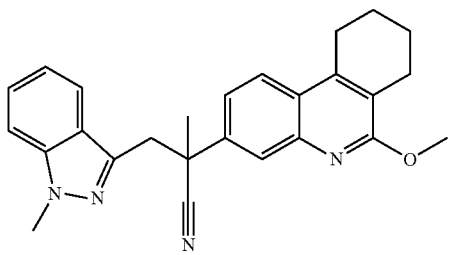 [SMILES: COc1nc2cc(C(C)(C#N)Cc3nn(C)c4ccccc34)ccc2c2c1CCCC2]

Potassium; 2-methyl-propan-2-olate (0.0011 mol) was added portionwise at 10° C. to a solution of intermediate 6 (0.0006 mol) and 3-chloromethyl-1-methyl-1H-indazole (0.0008 mol) in THF (5 mL) under N$_2$ flow. The mixture was stirred at room temperature for 5 hours, poured out into ice water and extracted with EtOAc. The organic layer was separated, dried (MgSO$_4$), filtered and the solvent was evaporated to dryness. The residue was crystallized from diethyl ether. The precipitate was filtered off and dried, yielding 0.15 g (65%) of intermediate 14.

Example A9

Preparation of Intermediate 15

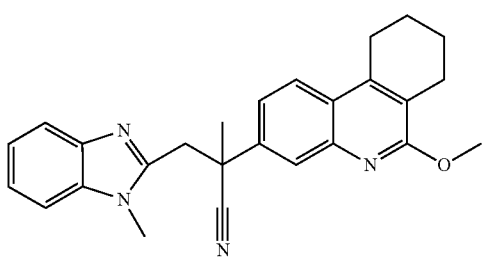 [SMILES: COc1nc2cc(C(C)(C#N)Cc3nc4ccccc4n3C)ccc2c2c1CCCC2]

Potassium; 2-methyl-propan-2-olate (0.0017 mol) was added portionwise at 10° C. to a solution of intermediate 6 (0.0006 mol) and 2-chloromethyl-1-methyl-1H-benzoimidazole (0.0008 mol) in THF (5 mL) under N$_2$ flow. The mixture was stirred at room temperature for 5 hours, poured out into ice water and extracted with EtOAc. The organic layer was separated, dried (MgSO$_4$), filtered and the solvent was evaporated to dryness. The residue was purified by column chromatography over silica gel (eluent: DCM 100 then DCM/ MeOH/NH$_4$OH 98/2/0.2; 3-5 μm). The pure fractions were collected and the solvent was evaporated, yielding 0.114 g (49%) of intermediate 15.

Example A10

Preparation of Intermediate 16

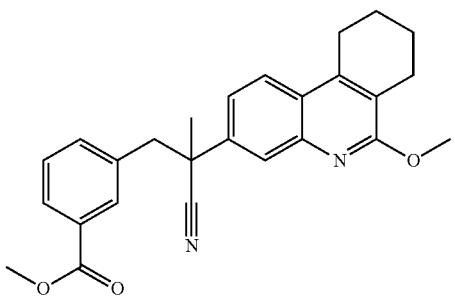

Potassium; 2-methyl-propan-2-olate (0.0049 mol) was added portionwise at 10° C. to a solution of intermediate 6 (0.0024 mol) and 3-bromomethyl-benzoic acid methyl ester (0.0036 mol) in THF (20 mL) under N$_2$ flow. The mixture was stirred at room temperature for 5 hours, poured out into ice water and extracted with EtOAc. The organic layer was separated, dried (MgSO$_4$), filtered and the solvent was evaporated to dryness. The residue was purified by column chromatography over silica gel (eluent: cyclohexane/EtOAc 80/20; 15-40 μm). The pure fractions were collected and the solvent was evaporated, yielding 0.392 g (39%) of intermediate 16.

Example A11

Preparation of Intermediate 17

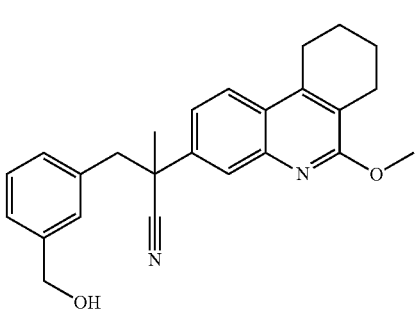 [SMILES: COc1nc2cc(C(C)(C#N)Cc3cccc(CO)c3)ccc2c2c1CCCC2]

A solution of intermediate 16 (0.0009 mol) in dry THF (3 mL) was added at 5° C. to a solution of aluminium lithium hydride (0.0009 mol) in dry THF (4 mL) under N$_2$ flow. The mixture was stirred at 5° C. for 1 hour. EtOAc then water were added slowly. The precipitate was removed by filtration through a layer of celite. The filtrate was extracted with EtOAc. The organic layer was washed with water, dried (MgSO₄), filtered and the solvent was evaporated to dryness, yielding 0.29 g (66%) of intermediate 17.

Example A12 a) Preparation of Intermediate 18

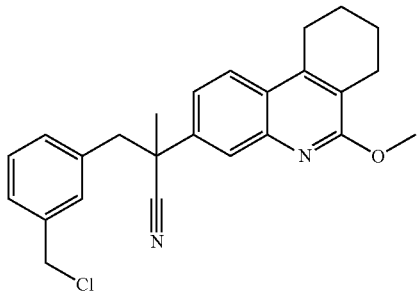

Thionyl chloride (0.09 mL) was added dropwise at 5° C. to a solution of intermediate 17 (0.0006 mol) in DCM (3 mL). The mixture was stirred at 5° C. for 1 hour, then stirred at room temperature for 3 hours and evaporated to dryness, yielding 0.22 g (95%) of intermediate 18, which was used without further purification in the next reaction step.

b) Preparation of Intermediate 19

Mixture of

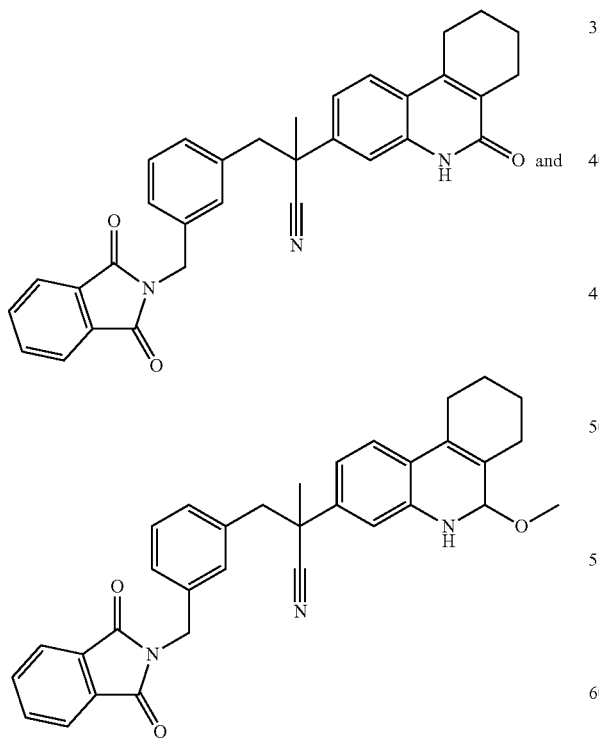

A mixture of intermediate 18 (0.0005 mol), isoindole-1,3-dione (0.0011 mol) and K₂CO₃ (0.0011 mol) in DMF (3 mL) was stirred at 100° C. for 4 hours, then cooled to room temperature, poured out into water and extracted with EtOAc. The organic layer was washed with water, dried (MgSO₄), filtered and the solvent was evaporated to dryness, yielding 0.32 g of intermediate 19, which was used without further purification in the next reaction step.

c) Preparation of Intermediate 20

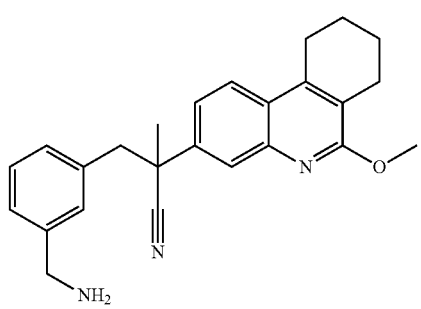 [SMILES: COc1nc2cc(C(C)(C#N)Cc3cccc(CN)c3)ccc2c2c1CCCC2]

Hydrazine monohydrate (0.0019 mol) was added dropwise to a solution of intermediate 19 (0.0006 mol) in ethanol (4 mL). The mixture was stirred at 80° C. for 4 hours, poured out into cold water and extracted with EtOAc. The organic layer was washed with water and brine, dried (MgSO₄), filtered and the solvent was evaporated to dryness. The residue was purified by flash column chromatography over silica gel (eluent: DCM/MeOH/NH₄OH from 98/2/0.2 to 88/12:1.2; 3-5 μm). The pure fractions were collected and the solvent was evaporated to dryness. The residue (0.034 g) was taken up in DCM and diethyl ether, yielding 0.03 g (13%) of intermediate 20, melting point: 80° C.

Example A13

Preparation of Intermediate 21

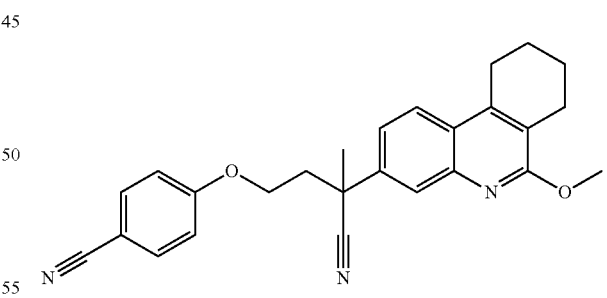

Potassium; 2-methyl-propan-2-olate (0.0011 mol) was added portionwise at 10° C. to a solution of intermediate 6 (0.0006 mol) and 4-(2-bromo-ethoxy)-benzonitrile (0.0008 mol) in THF (5 mL) under N₂ flow. The mixture was stirred at room temperature overnight, poured out into ice water and extracted with EtOAc. The organic layer was separated, dried (MgSO₄), filtered and the solvent was evaporated to dryness. The residue was purified by column chromatography over silica gel (eluent: DCM/cyclohexane 80/20; 3-5 μm). The pure fractions were collected and the solvent was evaporated, yielding 0.12 g (52%) of intermediate 21.

Example A14 a) Preparation of Intermediate 22

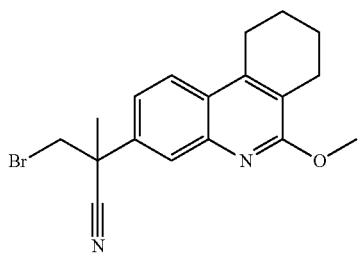 [SMILES: COc1nc2cc(C(C)(C#N)CBr)ccc2c2c1CCCC2]

A solution of intermediate 6 (0.0019 mol) in 1,2-dimethoxy-ethane (1 mL) was added dropwise at 10° C. to a solution of potassium; 2-methyl-propan-2-olate (0.0022 mol) in 1,2-dimethoxy-ethane (3 mL) under $N_2$ flow. The solution was stirred at room temperature for 1 hour. Dibromomethane (0.0028 mol) was added. The mixture was stirred at room temperature for 2 hours, poured out into cold water and extracted with EtOAc. The organic layer was washed with water, dried ($MgSO_4$), filtered and the solvent was evaporated to dryness, yielding 0.5 g (74%) of intermediate 22, which was used without further purification in the next reaction step.

b) Preparation of Intermediate 23

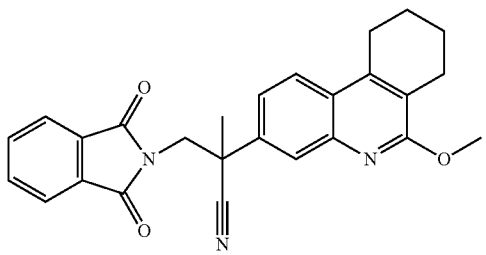 [SMILES: COc1nc2cc(C(C)(C#N)CN3C(=O)c4ccccc4C3=O)ccc2c2c1CCCC2]

A mixture of intermediate 22 (0.0014 mol) and phtalimide, potassium derivative (0.0017 mol) in DMF (10 mL) was stirred at 140° C. overnight, poured out into cold water and extracted with EtOAc. The organic layer was washed with water, dried ($MgSO_4$), filtered and the solvent was evaporated to dryness, yielding 0.44 g (74%) of intermediate 23, which was used without further purification in the next reaction step.

c) Preparation of Intermediate 24

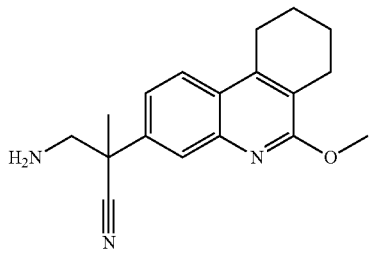 [SMILES: COc1nc2cc(C(C)(C#N)CN)ccc2c2c1CCCC2]

A mixture of intermediate 23 (0.001 mol) and hydrazine monohydrate (0.01 mol) in ethanol (10 mL) was stirred at 80° C. for 3 hours, then cooled to room temperature, poured out into cold water and extracted with EtOAc. The organic layer was separated, dried ($MgSO_4$), filtered and the solvent was evaporated to dryness, yielding 0.3 g (98%) of intermediate 24 (oil).

d) Preparation of Intermediate 25

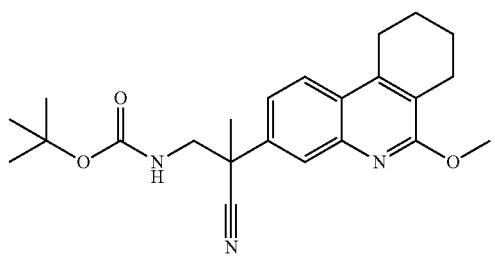 [SMILES: COc1nc2cc(C(C)(C#N)CNC(=O)OC(C)(C)C)ccc2c2c1CCCC2]

Di-tert-butyl-dicarbonate (0.0011 mol) was added at 10° C. to a solution of intermediate 24 (0.001 mol) in THF (14 mL) under $N_2$ flow. The mixture was stirred at room temperature for 5 hours, poured out into cold water and extracted with DCM. The organic layer was washed with water, dried ($MgSO_4$), filtered and the solvent was evaporated to dryness. The residue was purified by column chromatography over silica gel (eluent:DCM 100 then DCM/MeOH/$NH_4OH$ 99/1/0.1; 3.4 μm). The pure fractions were collected and the solvent was evaporated to dryness, yielding 0.197 g (47%) of intermediate 25 (oil).

e) Preparation of Intermediate 26

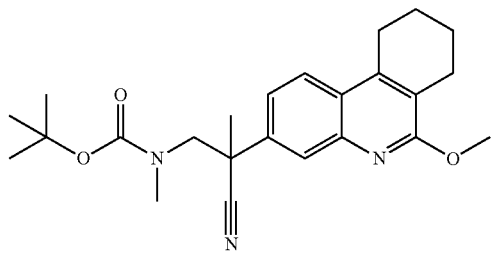 [SMILES: COc1nc2cc(C(C)(C#N)CN(C)C(=O)OC(C)(C)C)ccc2c2c1CCCC2]

Sodium hydride (0.0006 mol) was added at 10° C. to a solution of intermediate 25 (0.0005 mol) in DMF (3 mL) under $N_2$ flow. The mixture was stirred at room temperature for 30 minutes. Iodomethane (0.0005 mol) was added. The solution was stirred at room temperature for 4 hours, poured out into cold water and extracted with EtOAc. The organic layer was washed with water, dried ($MgSO_4$), filtered and the solvent was evaporated to dryness, yielding 0.14 g (71%) of intermediate 26 (oil).

f) Preparation of Intermediate 27

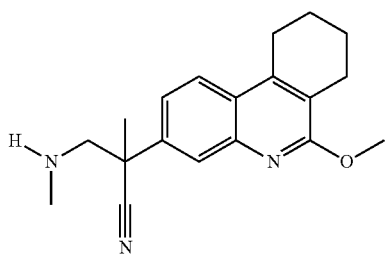 [SMILES: CNCC(C)(C#N)c1ccc2c3c(c(OC)nc2c1)CCCC3]

Trifluoro-acetic acid (0.0168 mol) was added at room temperature to a solution of intermediate 26 (0.0003 mol) in DCM (8 mL). The mixture was stirred at room temperature for 4 hours, poured out into cold water, basified with NH$_4$OH and extracted with DCM. The organic layer was separated, dried (MgSO$_4$), filtered and the solvent was evaporated to dryness. The residue was purified by flash column chromatography over silica gel (eluent: from DCM 100 to DCM/MeOH/NH$_4$OH 98/2/0.1). The pure fractions were collected and the solvent was evaporated to dryness, yielding 0.07 g (71%) of intermediate 27 (oil).

g) Preparation of Intermediate 28

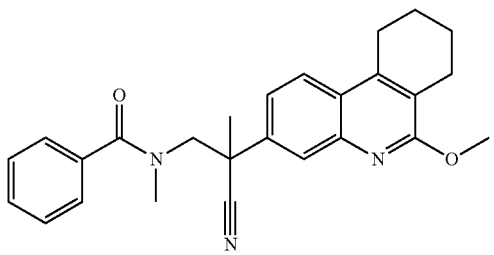 [SMILES: COc1nc2cc(C(C)(C#N)CN(C)C(=O)c3ccccc3)ccc2c2c1CCCC2]

Benzoyl chloride (0.0002 mol) was added at 10° C. to a solution of triethylamine (0.0002 mol) and intermediate 27 (0.0001 mol) in DCM (1.5 mL) under N$_2$ flow. The mixture was stirred at 10° C. for 3 hours, poured out into cold water and extracted with DCM. The organic layer was washed with water, dried (MgSO$_4$), filtered and the solvent was evaporated to dryness, yielding 0.074 g of intermediate 28.

Example A15

Preparation of Intermediate 29

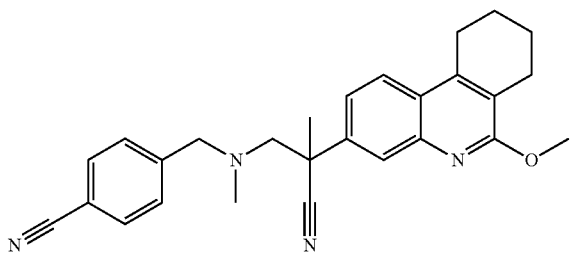

4-bromomethyl-benzonitrile (0.0002 mol) was added at 10° C. to a solution of intermediate 27 (0.0001 mol) and triethylamine (0.0002 mol) in DCM (2 mL) under N$_2$ flow. The mixture was stirred at 10° C. for 3 hours, then cooled to room temperature, poured out into cold water and extracted with DCM. The organic layer was washed with water, dried (MgSO$_4$), filtered and the solvent was evaporated to dryness, yielding 0.026 g (42%) of intermediate 29 (oil).

Example A16

Preparation of Intermediate 30

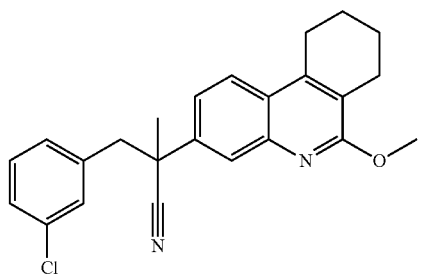 [SMILES: COc1nc2cc(C(C)(C#N)Cc3cccc(Cl)c3)ccc2c2c1CCCC2]

Potassium; 2-methyl-propan-2-olate (0.0011 mol) was added portionwise at 10° C. to a solution of intermediate 6 (0.00056 mol) and 1-bromomethyl-3-chlorobenzene (0.0008 mol) in THF (10 mL) under N$_2$ flow. The mixture was stirred at room temperature for 5 hours, poured out into ice water and extracted with EtOAc. The organic layer was separated, dried (MgSO$_4$), filtered and the solvent was evaporated to dryness, yielding 0.245 g (99%) of intermediate 30.

B. Preparation of the Compounds

Example B1 a) Preparation of Compound 1

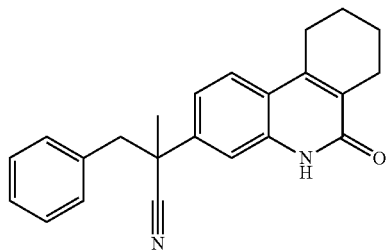 [SMILES: CC(C#N)(Cc1ccccc1)c1ccc2c3c(c(=O)[nH]c2c1)CCCC3]

HCl 3N (620 μL) was added to a solution of intermediate 7 ((0.0003 mol) in 1,4-dioxane (2.5 mL). The mixture was stirred at 80° C. for 18 hours, then cooled to room temperature, quenched with NaOH (0.1 M) and extracted with EtOAc. The organic layer was washed with brine, dried (MgSO$_4$), filtered and the solvent was evaporated under reduced pressure. The residue was purified by column chromatography over silica gel (eluent: petroleum ether/EtOAc 50/50). The pure fractions were collected and the solvent was evaporated, yielding 0.0238 g (22%) of compound 1.

b) Preparation of Compound 2 and 3

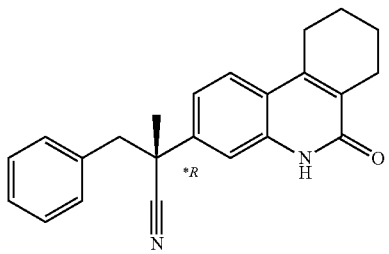

(enantiomer A)/compound 2

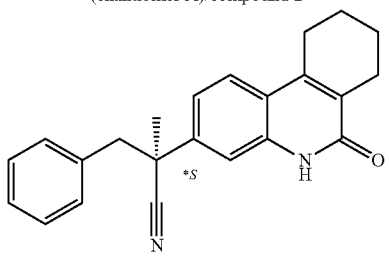

(enantiomer B)/compound 2

A solution of intermediate 7b (0.0004 mol) in HCl 3N (3 mL) and 1,4-dioxane (3 mL) was stirred at 80° C. for 5 hours, then cooled to room temperature. The precipitate was filtered, washed with water, then with diethyl ether and dried in vacuo, yielding 0.09 g (78%) of compound 3, melting point: 250° C.; $[\alpha]_D^{20}$=+89.87 (DMF; c=0.375).

A solution of intermediate 7a (0.0003 mol) in HCl 3N (3 mL) and 1,4-dioxane (3 mL) was stirred at 80° C. for 5 hours, then cooled to room temperature. The precipitate was filtered, washed with water, then with diethyl ether and dried in vacuo, yielding 0.083 g (75%) of compound 2, melting point: 245° C.; $[\alpha]_D^{20}$=−94.78 (DMF; c=0.35).

Example B2

Preparation of Compound 4

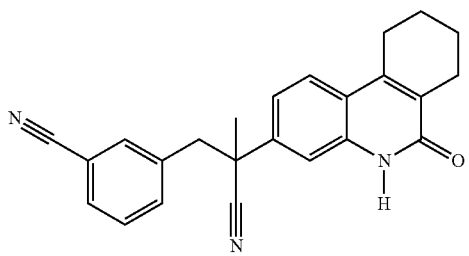 [SMILES: CC(C#N)(Cc1cccc(C#N)c1)c1ccc2c3c(c(=O)[nH]c2c1)CCCC3]

HCl 3N (620 μL) was added to a solution of intermediate 8 (0.0002 mol) in 1,4-dioxane (2.5 mL). The mixture was stirred at 80° C. for 18 hours, then cooled to room temperature, quenched with NaOH (0.1 M) and extracted with EtOAc. The organic layer was washed with brine, dried (MgSO$_4$), filtered and the solvent was evaporated under reduced pressure. The residue was purified by column chromatography over silica gel (eluent: cyclohexane/EtOAc 25/75). The pure fractions were collected and the solvent was evaporated, yielding 0.01 g (14%) of compound 4.

Example B3 a) Preparation of Compound 5

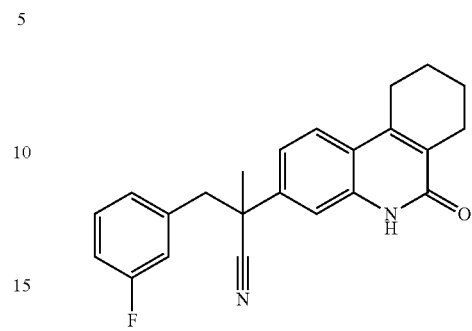

A mixture of intermediate 9 (0.0006 mol) in HCl 3N (2 mL) and 1,4-dioxane (4 mL) was stirred at 80° C. for 5 hours, then cooled to room temperature, filtered, washed with water, then with diethyl ether and dried in vacuo. The residue and the filtrate were mixed together and taken up in EtOAc and K$_2$CO$_3$ 10%. The organic layer was separated, dried (MgSO$_4$), filtered and the solvent was evaporated to dryness. The residue was crystallized from diethyl ether. The precipitate was filtered off and dried, yielding 0.049 g of compound 5, melting point: 217° C.

b) Preparation of Compound 5a and 5b

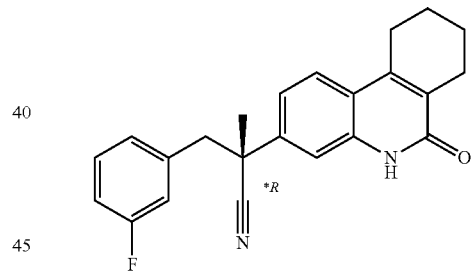

(enantiomer A)/compound 5a

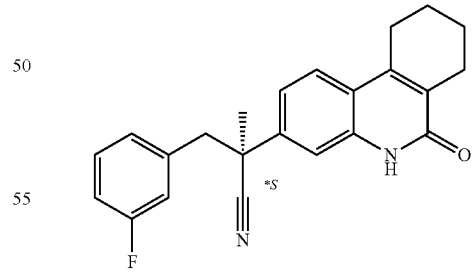

(enantiomer B)/compound 5b

A solution of intermediate 9 (0.0009 mol) in HCl 3N (6 mL) and 1,4-dioxane (6 mL) was stirred at 80° C. for 4 hours, then cooled to room temperature. The precipitate was filtered, washed with water and diethyl ether and dried. The residue was separated into its enantiomers by column chromatography (eluent: MeOH 100). Two fractions were collected and the solvent was evaporated. Enantiomer A was crystallized from diethyl ether. The precipitate was filtered off and dried, yielding 0.102 g (32%) of compound 5a, melting point 226° C.; $[\alpha]_D^{20}$=+90.7 (DMF; c=0.34). Enantiomer B was crystallized from diethyl ether. The precipitate was filtered off and dried, yielding 0.098 g (31%) of compound 5b, melting point 222° C.; $[\alpha]_D^{20}$=−82.09 (DMF; c=0.335).

Example B4

Preparation of Compound 6

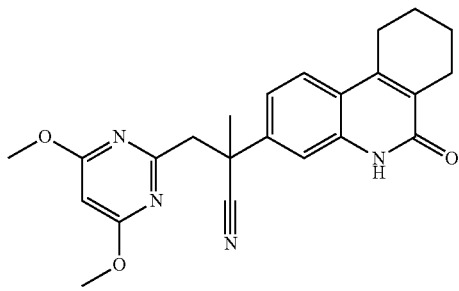 [SMILES: COc1cc(OC)nc(CC(C)(C#N)c2ccc3c4c(c(=O)[nH]c3c2)CCCC4)n1]

Potassium; 2-methyl-propan-2-olate (0.0008 mol) was added portionwise at 10° C. to a solution of intermediate 10 (0.0003 mol) and 2-(chloromethyl)-4,6-dimethoxypyrimidine (0.0008 mol) in THF (5 mL) under N2 flow. The mixture was stirred at room temperature overnight, poured out into ice water and extracted with EtOAc. The organic layer was separated, dried (MgSO$_4$), filtered and the solvent was evaporated to dryness. The residue was crystallized from DIPE. The precipitate was filtered off and dried, yielding 0.056 g (43%) of compound 6, melting point: 193° C.

Example B5

Preparation of Compound 7

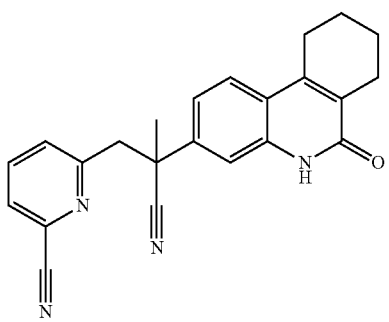 [SMILES: CC(C#N)(Cc1cccc(C#N)n1)c1ccc2c3c(c(=O)[nH]c2c1)CCCC3]

A solution of intermediate 11 (0.0006 mol) in HCl 3N (3 mL) and 1,4-dioxane (3 mL) was stirred at 80° C. for 4 hours, then cooled to room temperature, basified with K$_2$CO$_3$ 10% and extracted with EtOAc. The organic layer was separated, dried (MgSO$_4$), filtered and the solvent was evaporated to dryness. The residue was crystallized from DIPE. The precipitate was filtered off and dried, yielding 0.16 g (66%) of compound 7, melting point 210° C.

Example B6

Preparation of Compound 8

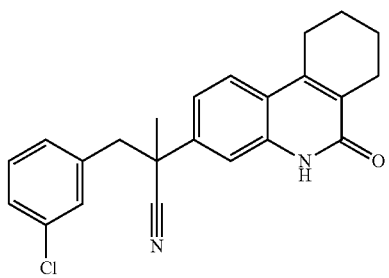 [SMILES: CC(C#N)(Cc1cccc(Cl)c1)c1ccc2c3c(c(=O)[nH]c2c1)CCCC3]

A solution of intermediate 30 (0.0005 mol) in HCl 3N (3 mL) and 1,4-dioxane (1.3 mL) was stirred at 80° C. for 4 hours, then cooled to room temperature. The precipitate was filtered, washed with water and diethyl ether and dried in vacuo, yielding 0.11 g (52%) of compound 8, melting point: 235° C.

Example B7

Preparation of Compound 9

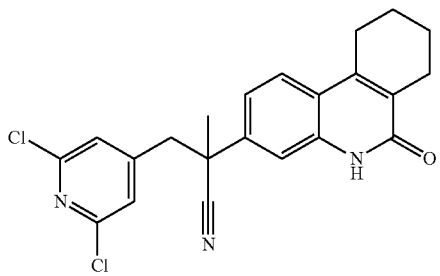 [SMILES: CC(C#N)(Cc1cc(Cl)nc(Cl)c1)c1ccc2c3c(c(=O)[nH]c2c1)CCCC3]

Potassium; 2-methyl-propan-2-olate (0.0016 mol) was added portionwise at 10° C. to a solution of intermediate 10 (0.0008 mol) and 2,6-dichloro-4-chloromethyl-pyridine (0.001 mol) in THF (15 mL) under N$_2$ flow. The mixture was stirred at room temperature overnight, poured out into ice water and extracted with EtOAc. The organic layer was separated, dried (MgSO$_4$), filtered and the solvent was evaporated to dryness. The residue was purified by column chromatography over silica gel (eluent: DCM/MeOH 98/2; 15-40 μm). The pure fractions were collected and the solvent was evaporated, yielding 0.07 g (21%) of compound 9, melting point: 212° C.

Example B8

Preparation of Compound 10

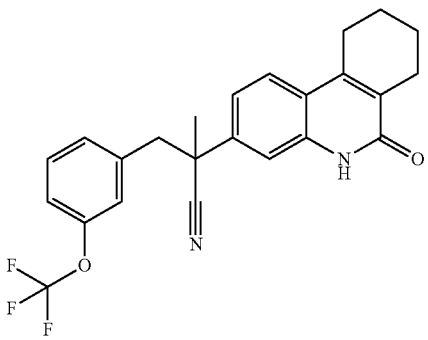

A solution of intermediate 12 (0.0005 mol) in HCl 3N (5 mL) and 1,4-dioxane (5 mL) was stirred at 80° C. overnight, then cooled to room temperature, poured out into ice water and extracted with EtOAc. The organic layer was separated, dried (MgSO$_4$), filtered and the solvent was evaporated to dryness. The residue was crystallized from diethyl ether. The precipitate was filtered off and dried, yielding 0.077 g (32%) of compound 10, melting point: 186° C.

Example B9

Preparation of Compound 11

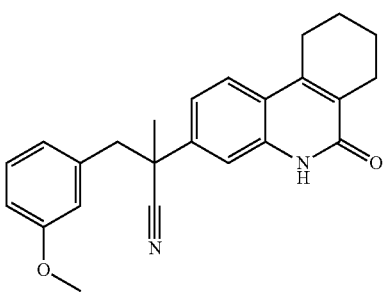 [SMILES: COc1cccc(CC(C)(C#N)c2ccc3c4c(c(=O)[nH]c3c2)CCCC4)c1]

A solution of intermediate 13 (0.0005 mol) in HCl 3N (5 mL) and 1,4-dioxane (5 mL) was stirred at 80° C. overnight, then cooled to room temperature. The precipitate was filtered, washed with water, then with diethyl ether and dried in vacuo, yielding 0.127 g (61%) of compound 11, melting point: 209° C.

Example B10

Preparation of Compound 12

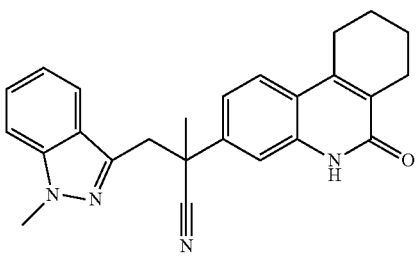 [SMILES: Cn1nc(CC(C)(C#N)c2ccc3c4c(c(=O)[nH]c3c2)CCCC4)c2ccccc21]

A solution of intermediate 14 (0.0003 mol) in HCl 3N (2 mL) and 1,4-dioxane (2 mL) was stirred at 80° C. for 5 hours, then cooled to room temperature. The precipitate was filtered, washed with water, then with diethyl ether and dried in vacuo, yielding 0.057 g (53%) of compound 12, melting point: 256° C.

Example B11

Preparation of Compound 13

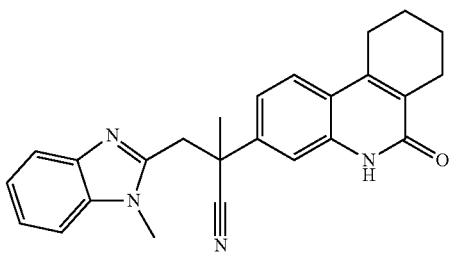 [SMILES: Cn1c(CC(C)(C#N)c2ccc3c4c(c(=O)[nH]c3c2)CCCC4)nc2ccccc21]

A solution of intermediate 15 (0.0003 mol) in HCl 3N (3 mL) and 1,4-dioxane (3 mL) was stirred at 80° C. for 5 hours, then cooled to room temperature, basified with K$_2$CO$_3$ 10% and extracted with EtOAc. The organic layer was separated, dried (MgSO$_4$), filtered and the solvent was evaporated to dryness. The residue was crystallized from diethyl ether. The precipitate was filtered off and dried in vacuo, yielding 0.065 g (61%) of compound 13, melting point: 260° C.

Example B12

Preparation of Compound 14

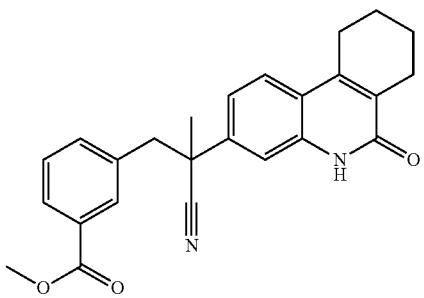 [SMILES: COC(=O)c1cccc(CC(C)(C#N)c2ccc3c4c(c(=O)[nH]c3c2)CCCC4)c1]

A solution of intermediate 16 (0.00007 mol) in HCl 3N (0.51 mL) and 1,4-dioxane (0.51 mL) was stirred at 80° C. for 4 hours, then poured out into cold water, basified with K$_2$CO$_3$ 10% and extracted with EtOAc. The organic layer was washed with water, dried (MgSO$_4$), filtered and the solvent was evaporated to dryness. The residue was taken up in DCM and diethyl ether. The precipitate was filtered off and dried, yielding 0.016 g (56%) of compound 14, melting point: 126° C.

Example B13

Preparation of Compound 15

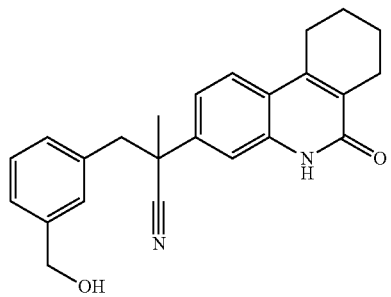 [SMILES: CC(C#N)(Cc1cccc(CO)c1)c1ccc2c3c(c(=O)[nH]c2c1)CCCC3]

A solution of intermediate 17 (0.00007 mol) in HCl 3N (0.51 mL) and 1,4-dioxane (0.51 mL) was stirred at 80° C. for 3 hours, then cooled to room temperature, basified with $K_2CO_3$ 10% and extracted with EtOAc. The organic layer was washed with water, dried ($MgSO_4$), filtered and the solvent was evaporated to dryness. The residue was crystallized from DIPE. The precipitate was filtered off and dried, yielding 0.0025 g (9%) of compound 15, melting point: 131° C.

Example B14

Preparation of Compound 16

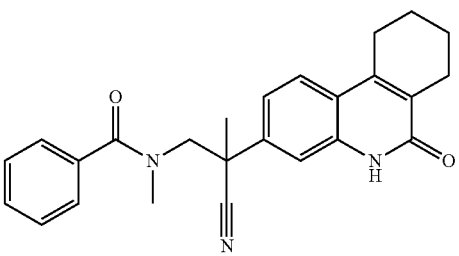

Hydrazine monohydrate (0.0019 mol) was added dropwise to a solution of intermediate 19 (0.0006 mol) in ethanol (4 mL). The mixture was stirred at 80° C. for 4 hours, poured out into cold water and extracted with EtOAc. The organic layer was washed with water and brine, dried ($MgSO_4$), filtered and the solvent was evaporated to dryness. The residue was purified by column chromatography over silica gel (eluent: DCM/MeOH/$NH_4OH$ from 98/2/0.2 to 88/12/1.2; 3.4 μm). The pure fractions were collected and the solvent was evaporated. The residue was taken up in DCM and diethyl ether. The precipitate was filtered off and dried, yielding 0.0173 g (7%) of compound 16, melting point: 80° C.

Example B15

Preparation of Compound 17

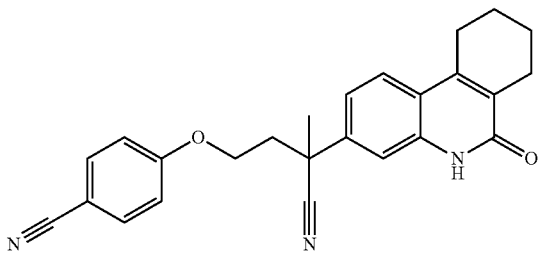 [SMILES: CC(C#N)(CCOc1ccc(C#N)cc1)c1ccc2c3c(c(=O)[nH]c2c1)CCCC3]

A solution of intermediate 21 (0.0003 mol) in HCl 3N (4 mL) and 1,4-dioxane (4 mL) was stirred at 80° C. for 4 hours, then cooled to room temperature and basified with $K_2CO_3$ 10%. The precipitate was filtered, washed with water, then with diethyl ether and dried, yielding 0.069 g (59%) of compound 17, melting point: 169° C.

Example B16

Preparation of Compound 18

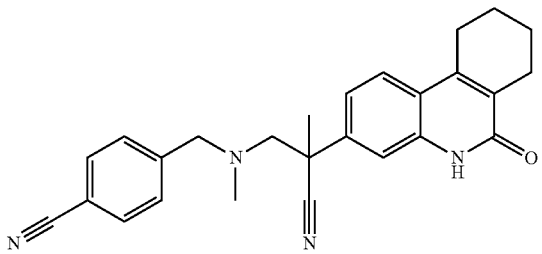 [SMILES: CN(Cc1ccc(C#N)cc1)CC(C)(C#N)c1ccc2c3c(c(=O)[nH]c2c1)CCCC3]

A solution of intermediate 28 (0.0002 mol) in HCl 3N (1.7 mL) and 1,4-dioxane (1.7 mL) was stirred at 80° C. for 4 hours, poured out into cold water and extracted with EtOAc. The organic layer was separated, dried ($MgSO_4$), filtered and the solvent was evaporated to dryness. The residue was crystallized from DIPE. The precipitate was filtered off and dried, yielding 0.032 g (44%) of compound 18, melting point: 248° C.

Example B17

Preparation of Compound 19

A solution of intermediate 29 (0.00007 mol) in HCl 3N (1 mL) and 1,4-dioxane (1 mL) was stirred at 80° C. for 4 hours, poured out into cold water, basified with K₂CO₃ 10% and extracted with EtOAc. The organic layer was washed with water, dried (MgSO₄), filtered and the solvent was evaporated to dryness. The residue was taken up in DCM and diethyl ether. The precipitate was filtered off and dried, yielding 0.025 g (87%) of compound 19, melting point: 254° C.

Table F-1 lists the compounds that were prepared according to one of the above Examples.

TABLE F-1

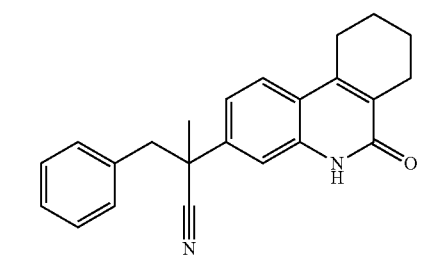 [SMILES: CC(C#N)(Cc1ccccc1)c1ccc2c3c(c(=O)[nH]c2c1)CCCC3]

Co. No. 1; Ex. [B1a]

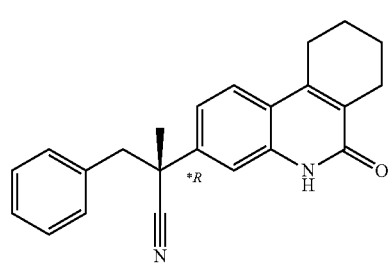 [SMILES: C[C@@](C#N)(Cc1ccccc1)c1ccc2c3c(c(=O)[nH]c2c1)CCCC3]

(enantiomer A); Co. No. 2; Ex. [B1]; mp. 245° C.

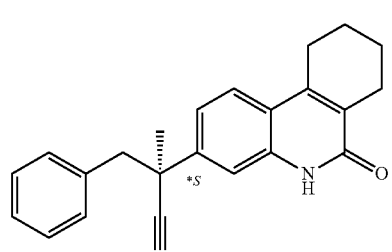

(enantiomer B); Co. No. 3; Ex. [B1]; mp. 250° C.

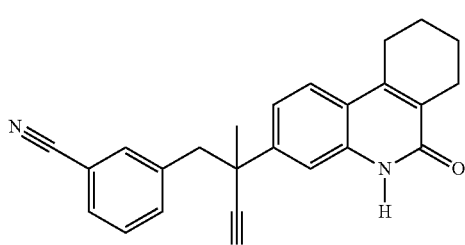

Co. No. 4; Ex. [B2]

TABLE F-1-continued

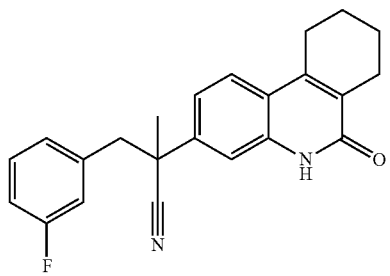 [SMILES: CC(C#N)(Cc1cccc(F)c1)c1ccc2c3c(c(=O)[nH]c2c1)CCCC3]

Co. No. 5; Ex. [B3a]; mp. 217° C.

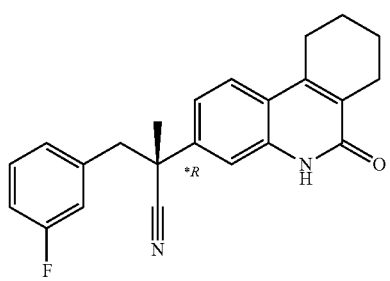 [SMILES: C[C@@](C#N)(Cc1cccc(F)c1)c1ccc2c3c(c(=O)[nH]c2c1)CCCC3]

(enantiomer A); Co. No. 5a; Ex. [B3]; mp. 226° C.

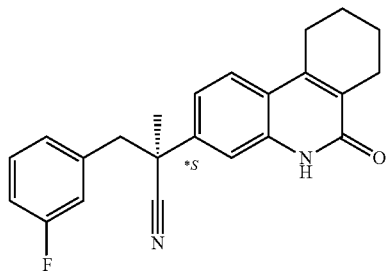

(enantiomer B); Co. No. 5b; Ex. [B3]; mp. 222° C.

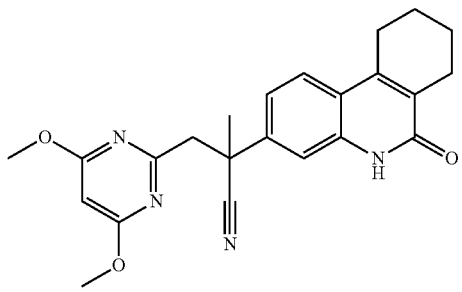 [SMILES: COc1cc(OC)nc(CC(C)(C#N)c2ccc3c4c(c(=O)[nH]c3c2)CCCC4)n1]

Co. No. 6; Ex. [B4]; mp. 193° C.

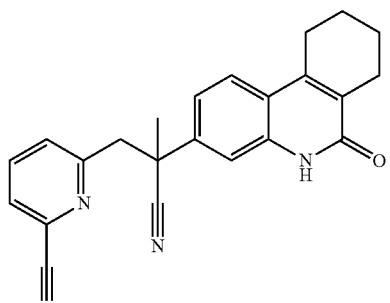

Co. No. 7; Ex. [B5]; mp. 210° C.

TABLE F-1-continued
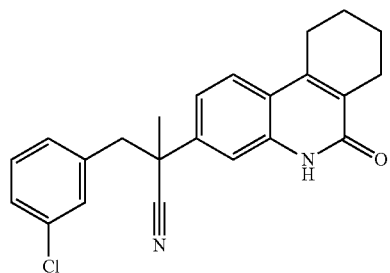 [SMILES: CC(C#N)(Cc1cccc(Cl)c1)c1ccc2c3c(c(=O)[nH]c2c1)CCCC3]
Co. No. 8; Ex. [B6]; mp. 235° C.
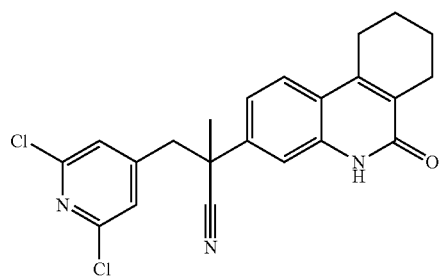 [SMILES: CC(C#N)(Cc1cc(Cl)nc(Cl)c1)c1ccc2c3c(c(=O)[nH]c2c1)CCCC3]
Co. No. 9; Ex. [B7]; mp. 212° C.
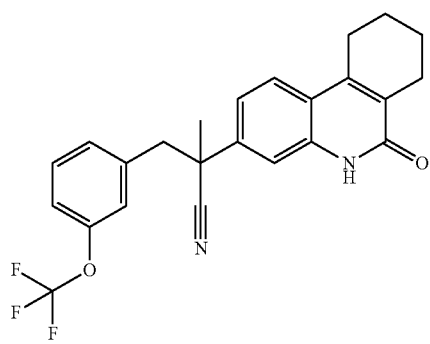 [SMILES: CC(C#N)(Cc1cccc(OC(F)(F)F)c1)c1ccc2c3c(c(=O)[nH]c2c1)CCCC3]
Co. No. 10; Ex. [B8]; mp. 186° C.
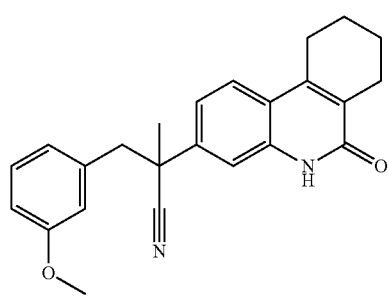 [SMILES: COc1cccc(CC(C)(C#N)c2ccc3c4c(c(=O)[nH]c3c2)CCCC4)c1]
Co. No. 11; Ex. [B9]; mp. 209° C.
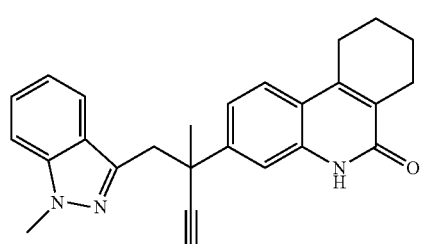
Co. No. 12; Ex. [B10]; mp. 256° C.
TABLE F-1-continued
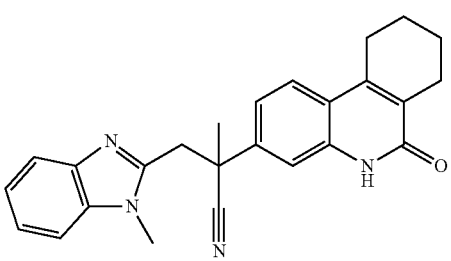 [SMILES: Cn1c(CC(C)(C#N)c2ccc3c4c(c(=O)[nH]c3c2)CCCC4)nc2ccccc21]
Co. No. 13; Ex. [B11]; mp. 260° C.
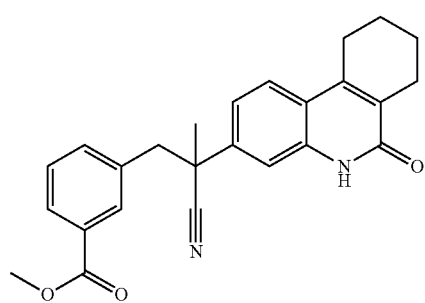 [SMILES: COC(=O)c1cccc(CC(C)(C#N)c2ccc3c4c(c(=O)[nH]c3c2)CCCC4)c1]
Co. No. 14; Ex. [B12]; mp. 126° C.
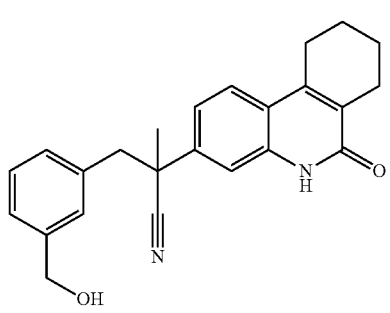 [SMILES: CC(C#N)(Cc1cccc(CO)c1)c1ccc2c3c(c(=O)[nH]c2c1)CCCC3]
Co. No. 15; Ex. [B13]; mp. 131° C.
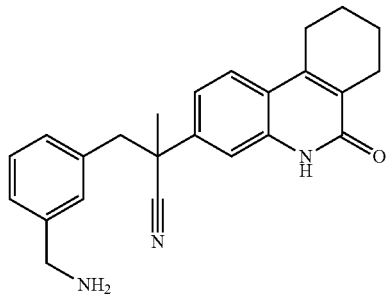 [SMILES: CC(C#N)(Cc1cccc(CN)c1)c1ccc2c3c(c(=O)[nH]c2c1)CCCC3]
Co. No. 16; Ex. [B14]; mp. 80° C.
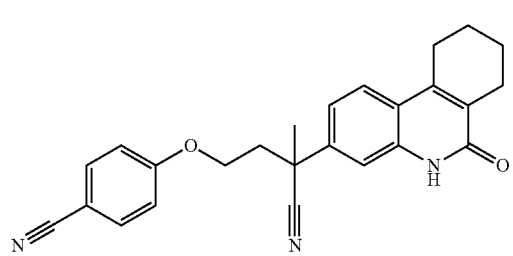 [SMILES: CC(C#N)(CCOc1ccc(C#N)cc1)c1ccc2c3c(c(=O)[nH]c2c1)CCCC3]
Co. No. 17; Ex. [B15]; mp. 169° C.

TABLE F-1-continued

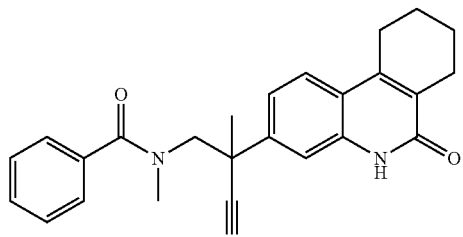

Co. No. 18; Ex. [B16]; mp. 248° C.

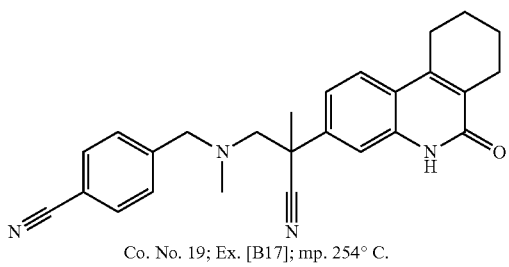

Co. No. 19; Ex. [B17]; mp. 254° C.

Analytical Part
LCMS
LCMS General Procedure

The HPLC measurement was performed using a Waters 1512 pump with a Waters diode-array detector (DAD) with a Gilson 215 autosampler and a column as specified in the respective methods below. Flow from the column was split to a MS spectrometer. Ionisation was either electrospray or APCI (atmospheric pressure chemical ionization) depending on type of compound.

Typical electrospray conditions use a capillary needle voltage of 3.5 kV and a cone voltage of 25 V. The source temperature was maintained at a temperature between 120-150° C. (the exact temperature was determined on a compound-by-compound basis). Typical APCI conditions use a corona discharge current of 17 µA, a cone voltage of 25 V, a desolvation temperature of 350° C. and the source temperature was maintained at a temperature between 140-160° C. (the exact temperature was determined on a compound-by-compound basis).

Mass spectra were acquired by scanning from 100 to 650 or 1000 when required, for example in 1 second using a dwell time of 0.1 sec. Nitrogen was used as the nebulizer gas.

LCMS—Procedure

In addition to general procedure: Reversed phase HPLC was carried out on a Waters Xterra MS 5µ C18 column (4.6× 100 mm; plus guard cartridge) with a flow rate of 2 ml/min. Two mobile phases (mobile phase A: water with 10 mM ammonium bicarbonate in ultra-pure water; mobile phase B: acetonitrile) were employed to run a gradient condition from 95% A to 95% B with a flow rate of 2 ml/min in 3.5 minutes and hold for 2 minutes. Typically, injection volumes of between 2 µl and 7 µl, inclusive were used.

TABLE 2

Analytical data - Retention time ($R_t$ in minutes), $(MH)^+$ peak.

| Co. Nr. | $R_t$ | $[M + H]^+$ |
|---|---|---|
| 1 | 3.65 | 343 |
| 4 | 3.44 | 368 |

C. Pharmacological Examples

C.1. In Vitro Scintillation Proximity Assay (SPA) for PARP-1 Inhibitory Activity Compounds of the present invention were tested in an in vitro assay based on SPA technology (proprietary to GE healthcare).

In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([$^3$H]-NAD$^+$) as ADP-ribosyl donor.

Histones (type II-A, supplier: Sigma) were biotinylated using the biotinylation kit of Amersham and stored aliquoted at −20° C. A stock solution of 100 mg/ml SPA poly(vinyl toluene) (PVT) beads (supplier: Amersham) was made in PBS. A stock solution of 61.6 nM [$^3$H]-NAD$^+$ was made by adding [$^3$H]-NAD$^+$ (0.1 mCi/ml, supplier: Perkin Elmer) to incubation buffer (50 mM Tris/HCl, pH 8; 0.2 mM DTT; 4 mM MgCl$_2$). A solution of 4 mM NAD$^+$ (supplier: Sigma) was made. Human PARP-1 enzyme was obtained from Trevigen. Biotinylated histones and PVT-SPA beads were mixed and pre-incubated for 30 minutes at room temperature. PARP-1 enzyme (concentration was lot dependent) was mixed with the nicked DNA and the mixture was pre-incubated for 30 minutes at 4° C. Equal parts of this histones/PVT-SPA beads solution and PARP-1 enzyme/DNA solution were mixed and 75 µl of this mixture together with 1 µl of compound in DMSO and 25 µl of [$^3$H]-NAD$^+$ was added per well into a 96-well microtiterplate. The final concentrations in the incubation mixture were 2 µg/ml for the biotinylated histones, 2 mg/ml for the PVT-SPA beads, 0.25 µg/ml for the nicked DNA and between 0.1-0.2 µg/ml for the PARP-1 enzyme. After incubation of the mixture for 20 minutes at room temperature, the reaction was terminated by adding 100 µl of 4 mM NAD$^+$ in water (final concentration 2 mM) and plates were mixed. The beads were sedimented by centrifugation (10 min, 800 rpm) and plates transferred to a TopCount-NXT™ (Packard) for scintillation counting, values were expressed as counts per minute (cpm). For each experiment, controls (containing PARP-1 enzyme and DMSO without compound), a blank incubation (containing DMSO but no PARP-1 enzyme, no DNA or compound) and samples (containing PARP-1 enzyme, DNA and compound dissolved in DMSO) were run in parallel. All compounds tested were dissolved and eventually further diluted in DMSO. A dose-response curve was made wherein the compounds were tested at concentrations between $10^{-5}$ M and $3\times10^{-9}$ M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the SPA assay. The tested compounds showed inhibitory activity at various concentrations (see Table-2).

C.2. In Vitro Scintillation Proximity Assay (SPA) for TANK-2 Inhibitory Activity Compounds of the present invention were tested in an in vitro assay based on SPA technology with Ni Flash plates (96 or 384 well).

In principle, the assay relies upon SPA technology for the detection of auto-poly(ADP-ribosyl)ation of TANK-2 protein using [$^3$H]-nicotinamide adenine dinucleotide ([$^3$H]-NAD$^+$) as ADP-ribosyl donor.

A stock solution of 100 nM [$^3$H]-NAD$^+$/NAD (0.1 mCi/ml, supplier: Perkin Elmer) and 25 µM NAD (Sigma) was made in assay buffer (60 mM Tris/HCl, pH 7.4; 0.9 mM DTT; 6 mM MgCl$_2$). The TANK-2 enzyme was produced as described in EP1238063 0.60 µl of assay buffer, together with 1 µl of compound in DMSO, 20 µl of [$^3$H]-NAD$^{+/-}$/NAD and 20 µl of TANK-2 enzyme (final concentration 8 µg/ml) was added per well into a 96-well Ni-coated flash plate (Perkin Elmer). After incubation of the mixture for 120 minutes at room temperature, the reaction was terminated by adding 60 µl of stop solution (42.6 mg NAD in 6 ml H$_2$O). The plates were covered with a plate sealer and placed in a TopCountNXT™ (Packard) for scintillation counting. Values were expressed as counts per minute (cpm). For each experiment, controls (containing TANK-2 enzyme and DMSO without compound), a blank incubation (containing DMSO but no TANK-2 enzyme or compound) and samples (containing TANK-2 enzyme and compound dissolved in DMSO) were run in parallel. All compounds tested were dissolved and eventually further diluted in DMSO. In first instance, compounds were tested at a concentration of $10^{-5}$ M. When the compounds showed activity at $10^{-5}$ M, a dose-response curve was made wherein the compounds were tested at concentrations between $10^{-5}$ M and $3 \times 10^{-8}$ M. In each test, the blank value was subtracted from both the control and the sample values. The control sample represented maximal TANK-2 enzyme activity. For each sample, the amount of cpm was expressed as a percentage of the mean cpm value of the controls. When appropriate, IC$_{50}$-values (concentration of the drug needed to reduce the TANK-2 enzyme activity to 50% of the control) were computed using linear interpolation between the experimental points just above and below the 50% level. Herein the effects of test compounds are expressed as pIC$_{50}$ (the negative log value of the IC$_{50}$-value). As reference compounds, 3-aminobenzamide and 4-amino-1,8-naphtalimide were included to validate the SPA assay. Herein the assay was described using 96-well plates. In the assay using 384-well plates the same final concentrations were used and volumes were adapted. If 96-well plate results were available these results were incorporated in Table-2, otherwise the results from the 384-well plate assay were shown.

Example C.4 Detection of Antiproliferative Activity

Human colon carcinoma HCT116 cells obtained from the ATCC were cultured in McCoy's 5A medium supplemented with 2 mM L-Glutamine, 50 µg/ml gentamicin and 10% heat inactivated fetal calf serum.

Human prostate cancer PC-3 cells obtained form the ATCC were cultured in HAM'S F12 medium supplemented with 1 mM Sodium Pyruvate, 1.5 g/L Sodium Bicarbonate, 50 µg/ml gentamicin, non-essential amino acids and 10% fetal calf serum.

Reagents Used in the Alamar Blue Assay

Resazurin was purchased from Aldrich (Prod. No. 199303). Potassium ferrocyanide, potassium ferricyanide, KH$_2$PO$_4$ and K$_2$HPO$_4$ were purchased from Sigma (Prod. Nos. P9387, P8131, P5655 and P8281, respectively).

Potassium Phosphate Buffer 0.1 M (PPB) was made as follows: 2.72 gram KH$_2$PO$_4$ and 13.86 gram K$_2$HPO$_4$ were dissolved in 500 ml milli-Q H$_2$O, the pH was adjusted to pH 7.4 and the volume was brought to 1 liter with milli-Q H$_2$O; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20× (vol/vol) in PPB and filter sterilising; the Alamar Blue solution could be kept at 4° C. for a maximum of 2 weeks.

Procedure of the Alamar Blue Assay

For experiments in 384 wells plates the cells were seeded at a density of $4.5 \times 10^3$ cells/ml in Falcon 384-well culture plates (Life Technologies, Merelbeke, Belgium), black with clear bottom, in 45 µl culture medium. Cells were allowed to adhere to plastic for 24 hours. The tested compound was pre-diluted (1/50 in culture medium) and 5 µl pre-diluted compound was added to the wells. Following 4-day incubation, 10 µl of the Alamar Blue solution was added to each well and the cells were further incubated for 4 hours (HCT116) or 24 hours (PC-3) at 37° C. The fluorescence intensity was measured for each well on a Fluorescence plate reader (Fluorskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, IC$_{50}$-values (concentration of the drug needed to reduce cell growth to 50% of the control) were computed using profit analysis for graded data (Finney, D. J., Probit Analyses, 2nd Ed. Chapter 10, Graded Responses, Cambridge University Press, Cambridge 1962). Herein the effects of tested compounds are expressed as pIC$_{50}$ (the negative log value of the IC$_{50}$ value) (see Table 3).

Example C.5 Polymerization Assay

The tubulin polymerization assay is an adaptation of an assay originally described by Bonne, D. et al. (J. Biol. Chem., 1985, 260:2819-25). The assay kit was purchased from Cytoskeleton, Inc. (catalogue number BK011) and the assay was performed as described by the supplier with the following modifications. The assay was run in a 384-well black Proxiplate (Perkin Elmer) and volumes were adapted accordingly. The reactions were carried out in a final volume of 10 µl. Compounds were added to 25 µl of the reaction mix in 96-well PP plates (Corning) on ice and 10 µl of this mixture was dispensed into duplicates of the 384-well Proxiplates pre-warmed to 37° C. in a Fluoroskan Ascent plate reader (Thermo Scientific). Fluorescence measurements were taken every minute for one hour. The maximum slope of each well was determined (linear regression through 4 consecutive points) and polymerization was calculated as a percentage of polymerization observed in the absence of compound. Compounds were first measured at a concentration of 20 µM and then at 5 µM for those showing more than 50% inhibition at 20

μM as compared to the polymerization observed in the absence of compound. Results are reported in Table F-2 as scores defined as: a compound showing 0 to 50% inhibition at 20 μM is reported as score 1; a compound showing more than 50% inhibition at 5 μM is reported as score 3. Score 2 compounds are defined as compound showing more than 50% inhibition at 20 μM and less than 50% inhibition at 5 μM.

Example C.6 Eb1 Comet (Microtubule Disruption) Assay

The Eb1 Comet assay relies on the detection of the Eb1 protein at the plus end of polymerizing microtubules (Mimori-Kiyosue, 2000) using indirect immunofluorescence. Disruption of microtubule dynamics through de-polymerization or stabilization results in a de-localization of Eb1 from the growing microtubule ends and this is visualized by the disappearance of Eb1 containing cytoplasmic foci.

Briefly, human prostate cancer PC3 cells obtained from the American Type Culture Collection were grown in 96-well plates (Greiner, cat. no. 655090) in HAM's F12 medium as recommended by the provider (ATCC). The cells were treated for 1 hour at 37° C. with compounds dissolved in DMSO (0.6% final DMSO concentration). The culture medium was then removed by aspiration and the cells were fixed by adding cold methanol (−20 C). After a 15 minutes incubation at −20° C., the cells were washed twice with DPBS (Gibco) containing 0.5% Triton X-100. Mouse Eb1 antibody (BD Transduction Laboratories, cat. no. 610534) was added to the cells (1/250 dilution in DPBS containing 1% BSA) and incubated overnight at room temperature. The antibody was subsequently removed and the cells washed twice with DPBS, 0.5% Triton X-100. Secondary goat anti-mouse antibody conjugated to Alexa 488 fluorescent dye (Molecular Probes) was added at a 1/500 dilution in DPBS, 1% BSA and incubated for 1 hour at 37° C. The cells were washed twice with DPBS, 0.5% Triton X-100 and then DPBS containing 0.5% Triton X-100 and 1/5000 Hoechst 33342 (Molecular Probes) was added. Microscopy based Eb1 foci visualization was carried out using an IN Cell Analyser 1000 (Amersham Biosciences) using a 20× objective. Compound dependent microtubule disruption was visually determined by the disappearance in Eb1 foci. The lowest active concentration (LAC) was determined as the concentration where Eb1 foci were absent in at least 50% of the treated cells. Herein the effects of tested compounds are expressed as pLAC (the negative log value of the LAC value) (see Table 3).

TABLE 3

| Co. No | in vitro SPA assay PARP-1 pIC50 | in vitro SPA assay TANK-2 pIC50 | Assay Tubulin Polymerization score | Cellular assay Eb1 pLAC | Cellular assay HCT116 pIC50 |
|---|---|---|---|---|---|
| 1 | 7.44 | 7.85 | 2 | | 6.45 |
| 2 | 7.33 | 7.43 | | | <5 |
| 3 | 7.26 | 7.48 | | | 6.80 |
| 4 | 9.03 | 7.76 | 2 | | 6.83 |
| 5 | 9.01 | 7.71 | 2 | 7 | 6.55 |
| 5a | 7.80 | 7.40 | | | <5 |
| 5b | 7.44 | 7.47 | | | 7.01 |
| 6 | 7.27 | 7.72 | 3 | 8 | 7.24 |
| 7 | 8.38 | 8.02 | 3 | 7.5 | 7.23 |
| 8 | 7.08 | 7.28 | 2 | | 6.81 |
| 9 | 7.20 | 6.35 | | | 6.80 |
| 10 | 6.66 | 7.23 | | | 6.73 |
| 11 | 7.06 | 7.45 | | | 6.81 |
| 12 | 7.34 | 7.37 | | | 6.75 |
| 13 | 7.38 | 7.37 | | | 6.57 |

TABLE 3-continued

| Co. No | in vitro SPA assay PARP-1 pIC50 | in vitro SPA assay TANK-2 pIC50 | Assay Tubulin Polymerization score | Cellular assay Eb1 pLAC | Cellular assay HCT116 pIC50 |
|---|---|---|---|---|---|
| 14 | 7.01 | 7.20 | | | 6.98 |
| 15 | 7.48 | 7.39 | | | 6.64 |
| 16 | 6.10 | 7.42 | | | 6.38 |
| 17 | 7.35 | 7.28 | 2 | | 6.69 |
| 18 | | | | | <5 |
| 19 | | 7.19 | | | 6.23 |

D. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:
1. A compound of formula (I),

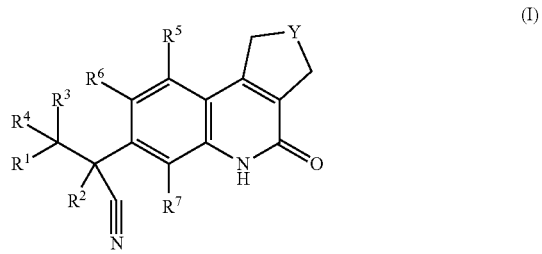

including a stereochemically isomeric form thereof;
wherein
Y is $CH_2$ or $CH_2$—$CH_2$;
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;

each aryl or Het can be substituted with one or two substituents each independently selected from halo, cyano $C_{1-6}$alkyl $C_{1-6}$alkyloxycarbonyl, —$C_{1-6}$alkylNR$^8$R$^9$, and —OR$^8$; or $R^1$ is a radical of formula

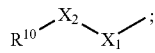
(b-1)

wherein $X_1$ is $CH_2$, NH or N—$CH_3$;

wherein $X_2$ is $CH_2$, C=O, O, NH or N—$CH_3$;

wherein $R^{10}$ is phenyl, pyridinyl, pyridazinyl or pyrimidinyl, wherein each phenyl, pyridinyl, pyridazinyl or pyrimidinyl can be substituted with one or two substituents each independently selected from halo, hydroxy, cyano, $C_{1-6}$alkyl, amino, polyhalo$C_{1-6}$alkyl or $C_{1-6}$alkyloxy; or $R^1$ is a radical of formula

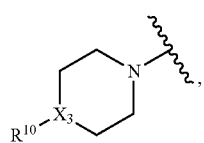
(b-2)

wherein $X_3$ is CH or N;

$R^2$ is methyl, ethyl, propyl or $C_{3-6}$cycloalkyl;

each $R^3$ and $R^4$ is hydrogen;

each $R^5$, $R^6$, and $R^7$ is hydrogen;

each $R^8$ and $R^9$ is independently selected from hydrogen, halo, $C_{1-6}$alkyl, or trihalo$C_{1-6}$alkyl;

a N-oxide form thereof, a pharmaceutically acceptable addition salt thereof or a solvate thereof.

2. A compound as claimed in claim 1 wherein

Y is $CH_2$—$CH_2$; aryl is phenyl; Het is pyridinyl, pyrimidinyl, benzimidazolyl or indazolyl;

each aryl or Het can be substituted with one or two substituents each independently selected from halo, cyano, $C_{1-6}$alkyl, $C_{1-6}$alkyloxycarbonyl, —$C_{1-6}$alkylNR$^8$R$^9$ or —OR$^8$; $X_1$ is $CH_2$ or N—$CH_3$; $X_2$ is $CH_2$, C=O or O; $R^{10}$ is phenyl which can be substituted with cyano; $R^2$ is methyl; $R^3$ and $R^4$ are hydrogen; $R^5$ and $R^6$ are hydrogen; $R^7$ is hydrogen; and each $R^8$ and $R^9$ is independently selected from hydrogen, halo, $C_{1-6}$alkyl or trihalo$C_{1-6}$alkyl.

3. A compound as claimed in claim 1 wherein

Y is $CH_2$—$CH_2$; $R^1$ is phenyl, pyridinyl or pyrimidinyl; each phenyl, pyridinyl or pyrimidinyl can be substituted with one or two substituents each independently selected from halo, cyano or $C_{1-6}$alkyloxy; $X_1$ is $CH_2$; $X_2$ is O; $R^{10}$ is phenyl substituted with cyano; $R^2$ is methyl; $R^3$ and $R^4$ are hydrogen; $R^5$ and $R^6$ are hydrogen; and $R^7$ is hydrogen.

4. A compound as claimed in claim 1 wherein the compound is selected from the following:

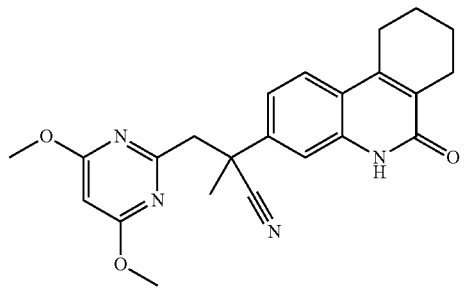

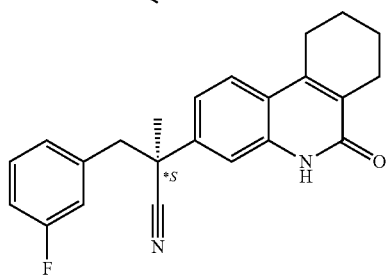
(Enantiomer B)

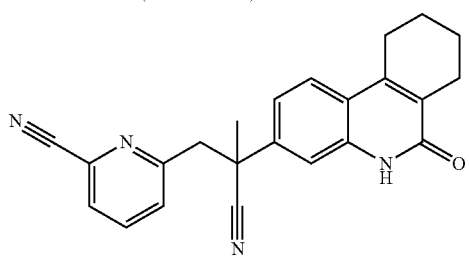

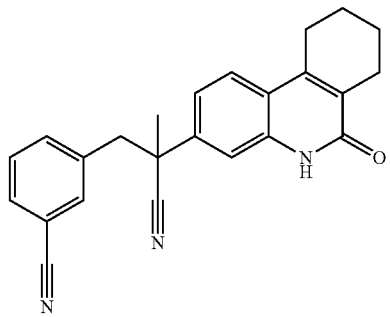

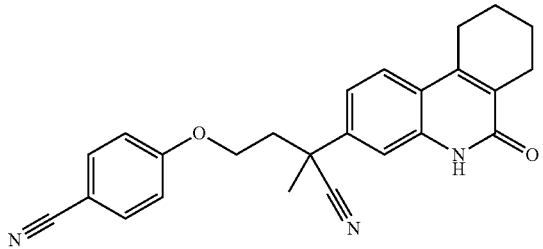

or a pharmaceutically acceptable addition salt thereof or a solvate thereof.

5. A pharmaceutical composition comprising a compound as claimed in claim 1 in a pharmaceutically acceptable carrier.

6. The composition of claim 5 comprising a combination with another anticancer agent.

7. A compound of formula (II)

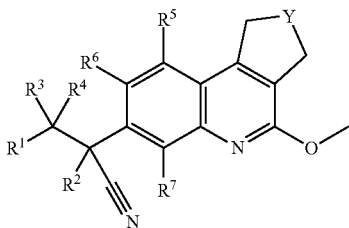

including a stereochemically isomeric form thereof;
wherein
Y is $CH_2$ or $CH_2$—$CH_2$,
$R^1$ is aryl or Het;
   wherein aryl is phenyl or naphthalenyl;
   wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
each aryl or Het can be substituted with one or two, substituents each independently selected from halo, cyano$C_{1-6}$alkyl, $C_{1-6}$alkyloxycarbonyl, hydroxy$C_{1-6}$alkyl, $C_{1-6}$alkyl-$NR^8R^9$, or —$OR^8$; or
$R^1$ is a radical of formula

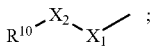 (b-1)

wherein $X_1$ is $CH_2$, NH or N—$CH_3$;
wherein $X_2$ is $CH_2$, C=O, O, NH or N—$CH_3$;
wherein $R^{10}$ is phenyl, pyridinyl, pyridazinyl or pyrimidinyl, wherein each phenyl, pyridinyl, pyridazinyl or pyrimidinyl can be substituted with one or two substituents each independently selected from halo, hydroxy, cyano, $C_{1-6}$alkyl, amino, polyhalo$C_{1-6}$alkyl or $C_{1-6}$alkyloxy; or
$R^1$ is a radical of formula

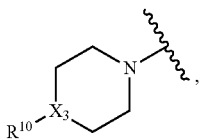 (b-2)

wherein $X_3$ is CH or N;
$R^2$ is methyl, ethyl, propyl or $C_{3-6}$cycloalkyl;
each $R^3$ and $R^4$ is independently selected from hydrogen, methyl, ethyl, propyl, hydroxy, trifluoromethyl, methyloxy; or $R^3$ and $R^4$ are taken together with the carbon atom to which they are attached to form a cyclopropyl ring or a radical of formula C(=O);
each $R^5$ and $R^6$ is hydrogen;
$R^7$ is hydrogen;
each $R^8$ and $R^9$ is independently selected from hydrogen, halo, $C_{1-6}$alkyl, $C_{2-6}$alkenyl, trihalo$C_{1-6}$alkyl;
a N-oxide form thereof, a pharmaceutically acceptable addition salt thereof or a solvate thereof.

8. A process for preparing a compound as claimed in claim 7, comprising
adding 2-methyl-2-propanol, potassium salt to an intermediate of formula (V) in the presence of an intermediate of formula (VI), wherein W is a leaving group, in a suitable solvent,

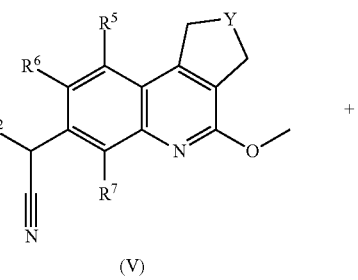 +

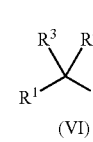

with the variables as defined in claim 7.

* * * * *